(12) United States Patent
Murray et al.

(10) Patent No.: US 7,700,307 B2
(45) Date of Patent: Apr. 20, 2010

(54) MITOCHONDRIAL STRESS-70 PROTEIN MARKERS FOR COLORECTAL CANCER

(75) Inventors: Graeme Ian Murray, Aberdeen (GB); Colin Matheson Telfer, Aberdeen (GB); William Thomas Melvin, Aberdeen (GB)

(73) Assignees: Auvation Limited, Aberdeen (GB); The University Court of the University of Aberdeen, Aberdeen (GB); Grampian Health Board (AKA NHS Grampian), Aberdeen (GB)

( * ) Notice: Subject to any disclaimer, the term of this patent is extended or adjusted under 35 U.S.C. 154(b) by 681 days.

(21) Appl. No.: 10/548,694

(22) PCT Filed: Mar. 8, 2004

(86) PCT No.: PCT/GB2004/000981

§ 371 (c)(1),
(2), (4) Date: Sep. 8, 2005

(87) PCT Pub. No.: WO2004/079368

PCT Pub. Date: Sep. 16, 2004

(65) Prior Publication Data

US 2006/0188883 A1 Aug. 24, 2006

(30) Foreign Application Priority Data

| Mar. 8, 2003 | (GB) | 0305342.8 |
| Mar. 8, 2003 | (GB) | 0305345.1 |
| Mar. 8, 2003 | (GB) | 0305346.9 |
| Mar. 8, 2003 | (GB) | 0305347.7 |
| Mar. 8, 2003 | (GB) | 0305348.5 |
| Mar. 8, 2003 | (GB) | 0305350.1 |
| Mar. 8, 2003 | (GB) | 0305351.9 |
| Mar. 8, 2003 | (GB) | 0305353.5 |
| Mar. 8, 2003 | (GB) | 0305382.4 |
| Mar. 8, 2003 | (GB) | 0305385.7 |
| Mar. 8, 2003 | (GB) | 0305387.3 |

(51) Int. Cl.
*G01N 33/574* (2006.01)
*G01N 33/53* (2006.01)

(52) U.S. Cl. ..................... 435/7.23; 435/7.1

(58) Field of Classification Search .................. None
See application file for complete search history.

(56) References Cited

U.S. PATENT DOCUMENTS 6,358,683 B1 3/2002 Collins
2002/0150569 A1* 10/2002 Hochstrasser et al. ..... 424/130.1
2003/0109434 A1* 6/2003 Algate et al. ................. 514/12

OTHER PUBLICATIONS

Takano et al (Experimental Cell Research, 1997, 237:38-45).*
Reymond et al (Electrophoresis, 1997, 18:2842-2848).*
Bermejo-Nogales et al, Comparative Biochemistry and Physiology, Part B, 149 (2008) 428-438.*
Dundas et al (J of Pathology, 2005, 205:74-81).*
Tockman et al (Cancer Res., 1992, 52:2711s-2718s).*
Shawn A. Ritchie et al., "Identification of the SRC pyrmidine-binding protein (Spy) as hnRNPK . . . ", Nucleic Acids Research, 31(5): 1502-1513 (2003).
Mahitosh Mandal et al., "Growth factors regulate heterogeneous nuclear ribonucleoprotein K . . . ", Journal of Biological Chemistry, 276(13): 9699-9704 (2001).
Saeyoung Park et al., "Proteome analysis of 5-fluorouracil-resistance-associated protein in human . . . ", Biotechnology Letters, 24(14): 1141-1145 (2002).
Judith A. McKay et al., "Application of the enrichment approach to identify putative markers of . . . ", International Journal of Oncology, 17(1): 153-158 (2000).
Claudia Ghigna et al., "Altered expression of heterogeneous nuclear ribonucleoproteins and SR factors . . . ", Cancer Research, 58(24): 5818-5824 (1998).
Annette M. Krecic et al., "hnRNP complexes: Composition, structure, and function", Current Opinion in Cell Biology, 11(3): 363-371 (1999).
Database Biosis Online, Biosciences Info Ser, Phil., PA; M.J. Matunis et al., "Characterization and Primary Structure . . . " Molecular Cell Biology, 12(1):164-171 (1992) [Abs].
S.R. Collie-Duguid et al., "Gene expression profiling of apoptosdis and cell cycle control in Dukes' C colon tumours", British Journal of Cancer, 88(S1): S48 (2003).

* cited by examiner

*Primary Examiner*—Laura B Goddard
(74) *Attorney, Agent, or Firm*—Patrick J. Hagan; Dann, Dorfman, Herrell and Skillman, P.C.

(57) ABSTRACT

Provided are previously uncharacterised markers of cancers, for example colorectal cancers, and uses of these as diagnostic and prognostic markers of cancers, and in particular colorectal cancers. The markers are SEQ ID NO: 1—hnRNP-K; SEQ ID NO:2—HMG-1; SEQ ID NO:3—proteasome subunit alpha type 1; SEQ ID NO:4—bifunctional purine biosynthesis protein; SEQ ID NO:5—ST11; SEQ ID NO:6—annex in IV; SEQ ID NO:7—60 kDa heat shock protein; SEQ ID NO:8—T complex protein 1 beta subunit; SEQ ID NO:9—T complex protein 1 epsilon subunit; SEQ ID NO: 10—mortalin; and SEQ ID NO: 11—TER-ATPase. The invention further provides related methods and materials for the use of the markers in therapeutic intervention in colorectal and other cancers e.g. to specifically target neoplastic cells without causing significant toxicity in healthy tissues, and to provide methods for the evaluation of the ability of candidate therapeutic compounds to modulate the biological activity of cancerous cells from the colon, rectum and other tissues.

4 Claims, No Drawings

MITOCHONDRIAL STRESS-70 PROTEIN MARKERS FOR COLORECTAL CANCER

BACKGROUND OF THE INVENTION

Cancer remains one of the leading causes of death in the Western world. Clinically, the treatment of human cancer currently involves the use of a broad variety of medical approaches, including surgery, radiation therapy and chemotherapeutic drug therapy (see, for example, the Oxford Textbook of Oncology, Souhami R L, Tannock I, Hohenberger P, and Horiot J-C (ed.s), 2nd edition, New York, N.Y., Oxford University Press, 2002).

A diverse group of chemotherapeutic agents are used in the treatment of human cancer, including the taxanes paclitaxel and docetaxel, the topoisomerase inhibitors etoposide, topotecan and irinotecan, the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, bis-diamminedichloroplatinum, azetidinylbenzoquinone; the plant alkaloids vincristine, vinblastine, vindesine, and VM-26; the antibiotics actinomycin-D, doxorubicin, daunorubicin, mithramycin, mitomycin C and bleomycin; and miscellaneous agents such as dacarbazine, mAMSA and mitoxantrone. However, some neoplastic cells develop resistance to specific chemotherapeutic agents or even to multiple chemotherapeutic agents, and some tumours are intrinsically resistant to certain chemotherapeutic agents. Such drug resistance or multiple drug resistance can theoretically arise from expression of genes that confer resistance to the agent, or from lack of expression of genes that make the cells sensitive to a particular anticancer drug.

It is well established that certain pathological conditions, including cancer, are characterized by the abnormal expression of certain molecules, and these molecules thus serve as "markers" for a particular pathological condition.

Apart from their use as diagnostic "targets", i.e. abnormal components that can be identified to diagnose the pathological condition, the molecules serve as reagents which can be used to generate diagnostic and/or therapeutic agents. An example of this, which is not intended to be limiting, is the use of markers of cancer to produce antibodies specific to a particular marker. A further non-limiting example is the use of a peptide which complexes with an MHC molecule, to generate cytolytic T cells against cells expressing the marker.

One particular cancer target of interest is colorectal cancer. Colorectal cancers are the third most common malignancies in the world, and amongst men in the European Union it is the second most common cause of cancer death after lung cancer. Although more than 90% of cases are curable when diagnosed at an early stage in development, the majority of patients with colorectal cancer present clinically when the tumour is at an advanced, metastatic stage. Consequently, the disease kills around 98,500 people every year in the EU (where less than 50% of patients survive 5 years after an initial diagnosis of colorectal cancer) and an estimated 437,000 people per annum worldwide. This problem of late diagnosis is compounded by the resistance of some patients' tumours to currently available chemotherapy; leading to a failure to respond to treatment. Such patients require earlier detection and more successful treatment of their illness, and to this end it is desirable to identify proteins whose expression is associated with cancerous cells, which may serve as diagnostic markers, prognostic indicators and therapeutic targets.

Colorectal cancer is a consequence of pathologic transformation of normal cells of the colonic epithelium to an invasive cancer, and may result from inherited mutation, spontaneous mutation or exposure to carcinogens in the bowel contents. The majority of cancers of the colorectum are adenocarcinomas (Jass & Morson, J. Clin. Pathol. 40: 1016-23, 1987), but questions remain concerning the true origins of colorectal carcinomas. Such carcinomas may arise both from within existing benign neoplasms ("adenomas"), in what has been termed the adenoma to carcinoma sequence (Muto et al, Cancer 30: 2251-70, 1975), but the majority of adenomas do not appear to progress to carcinoma and indeed may even regress (Knoemschild, Surg. Forum XIV: 137-8, 1963). Alternatively carcinomas may arise de novo from areas of generalised dysplasia without an adenomatous stage. Clinical evidence supports the identification of environment, diet, age and sex as risk factors for colorectal cancer, but the lack of confirmed involvement of these factors in all cases suggests an underlying genetic basis for colorectal tumour formation. Several genetic alterations have been implicated in development of colorectal cancer, including mutations in tumour-suppressor genes, proto-oncogenes and DNA repair genes (reviewed by Robbins & Itzkowitz, Med Clin North Am 86:1467-95, 2002; Fearnhead et al, Br Med Bull 64: 27-43, 2002). For example, WO 0077252 identifies the Barx2 gene as a candidate tumour suppressor implicated in ovarian and colorectal cancer.

One of the earliest detectable events, which may be the initiating event in colorectal tumourigenesis, is inactivating mutation of both alleles of the adenomatous polyposis coli (APC) tumour suppressor gene. Other implicated genes include MCC, p53, DCC (deleted in colorectal carcinoma), and genes in the TGF-beta signalling pathway. Tumour specific patterns of expression have also been demonstrated for a number of proteins in colorectal tissues, and these proteins are undergoing evaluation as diagnostic and therapeutic targets. One such protein is carcinoembryonic antigen (CEA), which is detectable in the majority of colorectal cancers but not in normal tissues (reviewed by Hammarstrom, Semin Cancer Biol 9: 67-81, 1999). CEA is immunologically detectable in the serum of colorectal cancer patients, and detection of CEA mRNA by RT-PCR can identify lymph node micrometastases, which are a prognostic indicator of a reduced chance of survival in colorectal cancers (Liefers et al, New England J. of Med. 339: 223-8, 1998). Another promising marker for colorectal cancer is minichromosome maintenance protein 2 (MCM2), which is being developed as a target for diagnosis from stool samples (Davies et al, Lancet 359: 1917-9, 2002).

At the present time, none of the protein markers under investigation are in routine clinical use, and further targets for diagnosis, prognosis and treatment are desirable. The current routine diagnostic test for colorectal cancer is the FOBT (Faecal Occult Blood Test), which is lacking in sensitivity and specificity. Evaluation of the effectiveness of this test indicates that it may fail to detect as many as 76% of suspicious growths (Lieberman et al, N Engl J Med; 345: 555-60, 2001). It also results in a large number of false positives and these patients require to undergo the unpleasant, invasive procedure of colonoscopy. Even when administered together these two procedures have been found to miss 24% of tumours and precancerous polyps. Currently the best candidates for new diagnostic tests are based on DNA analysis, but these have at best a 50% detection rate.

It will be appreciated from the forgoing that the provision of novel specific, reliable markers that are differentially expressed in normal and transformed tissues (such as colorectal tissue) would provide a useful contribution to the art. Such markers could be used inter alia in the diagnosis of cancers such as colorectal cancer, the prediction of the onset of cancers such as colorectal cancer, or the treatment of cancers such as colorectal cancer.

SUMMARY OF THE INVENTION

The present inventors have used specific proteomics approaches to identify proteins that are expressed in cancer cells but not in normal tissues. The target proteins of the present invention are listed in Table 2 and discussed in Example 2 herein.

Each marker has been identified by up-regulation of expression in colorectal tumour samples, an observation not previously made in this tissue type for any of these markers.

Previously, proteome studies have proven to be of limited success in identifying such markers. W09842736 and W09843091 do disclose certain differentially-expressed protein markers identified by proteomic analysis of clinical samples following laborious processing intended to enrich tumour epithelial cells by removing stromal cells and connective tissue contaminants. However, more recently, a proteomic comparison of murine normal and neoplastic colon tissues identified no statistically significant differences in protein expression patterns (Cole et al, Electrophoresis 21: 1772-81, 2000).

After the presently claimed priority date, the following studies were published relating to some of the markers disclosed herein: Kuniyasu H, Chihara Y, Kondo H, Ohmori H, Ukai R (2003) Amphoterin induction in prostatic stromal cells by androgen deprivation is associated with metastatic prostate cancer. *Oncol Rep.* 10(6): 1863-8; Cappello F, Bellafiore M, Palma A, David S, Marciano V, Bartolotta T, Sciume C, Modica G, Farina F, Zummo G, Bucchieri F. (2003) 60 KDa chaperonin (HSP60) is over-expressed during colorectal carcinogenesis. *European Journal of Histochemistry* 47 (2): 105-10; Yamamoto S, Tomita Y, Hoshida Y, Sakon M, Kameyama M, Imaoka S, Sekimoto M, Nakamori S, Monden M, Aozasa K. (2004) Expression of valosin-containing protein in colorectal carcinomas as a predictor for disease recurrence and prognosis. *Clinical Cancer Research* 10(2): 651-7.

Other publications concerning the present markers are discussed in Example 2 herein.

Accordingly, the present invention describes the use of the target proteins listed in Table 2 (which may be referred to hereinafter as "the target proteins of the present invention") as markers of cancer, and provides methods for their use in such applications.

As discussed in detail below, the target proteins of the present invention are of particular use inter alia as diagnostic and prognostic markers of cancers, and in particular colorectal cancers. As with known markers, they may be used for example to assist diagnosing the presence of cancer at an early stage in the progression of the disease and predicting the likelihood of clinically successful outcome, particularly with regard to the sensitivity or resistance of a particular patient's tumour to a chemotherapeutic agent or combinations of chemotherapeutic agents. Furthermore these targets can be used for therapeutic intervention in colorectal and other cancers e.g. to specifically target neoplastic cells without causing significant toxicity in healthy tissues, and to provide methods for the evaluation of the ability of candidate therapeutic compounds to modulate the biological activity of cancerous cells from the colon, rectum and other tissues.

Thus the present invention relates to the diagnosis and treatment of cancer, and specifically to the discrimination of neoplastic cells from normal cells on the basis of over-expression of specific tumour antigens and the targeting of treatment through exploitation of the differential expression of these antigens within neoplastic cells. The invention specifically relates to the detection of one or more proteins ("target proteins") that are over-expressed in neoplastic cells compared with the expression in pathologically normal cells (see Table 2). Furthermore the invention provides evidence for up-regulation of expression of this target in tumour cells where this has not previously been reported. Accordingly, this protein, as well as nucleic acid sequences encoding this protein, or sequences complementary thereto, can be used as a cancer marker useful in diagnosing or predicting the onset of a cancer such as colorectal cancer, monitoring the efficacy of a cancer therapy and/or as a target of such a therapy.

The invention in particular relates to the discrimination of neoplastic cells from normal cells on the basis of the over-expression of a target protein of the present invention, or the gene that encodes this protein. To enable this identification, the invention provides a pattern of expression of a specific protein, the expression of which is increased in neoplastic cells in comparison to normal cells. The invention provides a variety of methods for detecting this protein and the expression pattern of this protein and using this information for the diagnosis and treatment of cancer.

Furthermore, it is contemplated that the skilled artisan may produce novel therapeutics for treating colorectal cancer which include, for example: antibodies which can be administered to an individual that bind to and reduce or eliminate the biological activity of the target protein in vivo; nucleic acid or peptidyl nucleic acid sequences which hybridize with genes or gene transcripts encoding the target proteins thereby to reduce expression of the target proteins in vivo; or small molecules, for example, organic molecules which interact with the target proteins or other cellular moieties, for example, receptors for the target protein, thereby to reduce or eliminate the biological activity of the target protein.

The invention therefore further provides methods for targeting of therapeutic treatments for cancers by directing treatment against this over-expressed protein. Methods for achieving this targeting may include, but are not limited to;

(i) conjugation of therapeutic drugs to a moiety such as an immunoglobulin or aptamer that specifically recognises the molecular structure of the target protein, (ii) exposure of the host immune system to the target protein or fragments thereof by immunisation using proteins, polypeptides, expression vectors or DNA vaccine constructs in order to direct the host immune system against neoplastic cells in which the target protein is over-expressed, (iii) modification of the biological activity of the target protein by small molecule ligands, (iv) exploitation of the biological activity of the target protein to activate prodrugs, (v) modulation of the expression of the target protein in cells by methods such as antisense gene silencing, use of small interfering RNA molecules, or the targeting of regulatory elements in the gene encoding the target protein or regulatory proteins that bind to these elements, (vi) specific modulation of the physical interaction of the target protein with other components of the cell, with for example a small molecule ligand or an immunoglobulin, in order to exert a therapeutic benefit The present invention thereby provides a wide range of novel methods for the diagnosis, prognosis and treatment of cancers, including colorectal cancer, on the basis of the differential expression of the target protein. These and other numerous additional aspects and advantages of the invention will become apparent to the skilled artisan upon consideration of the following detailed description of the invention.

DETAILED DESCRIPTION OF THE PRESENT INVENTION

In the studies disclosed herein, proteomic analysis was applied to colorectal samples from a clinical tissue bank into which have been collected both tumour and pathologically normal (disease-free) tissues from each individual donor. Using a process whereby proteins are recovered from frozen sections of donor tissues selected from a bank of fresh frozen tissues on the basis of optimal tumour histology and cellularity, it was possible to derive the protein expression profiles of carefully selected sets of normal colon tissue and advanced (Duke's C stage) colorectal carcinomas selected from 16 patients. Comparison of the protein expression "fingerprints" of the tumour and normal tissue sets revealed differences that arise as a result of the disease process. Table 1 provides details of proteins identified by these means whose up-regulation in colorectal tumour tissues has previously been reported. Table 2 provides details of proteins identified by these means whose up-regulation in colorectal tumour tissues has not been previously demonstrated and thereby provides the basis of the present invention.

The objective of the present study was to identify new targets for cancer diagnosis and therapy. Accordingly, a first aspect of the present invention provides a method for the identification of cancer cells, which method comprises determining the expression of the target protein of the invention in a sample of tissue from a first individual and comparing the pattern of expression observed with the pattern of expression of the same protein in a second clinically normal tissue sample from the same individual or a second healthy individual, with the presence of tumour cells in the sample from the first individual indicated by a difference in the expression patterns observed.

More specifically, the invention provides a diagnostic assay for characterising tumours and neoplastic cells, particularly human neoplastic cells, by the differential expression of the target protein whereby the neoplastic phenotype is associated with, identified by and can be diagnosed on the basis thereof. This diagnostic assay comprises detecting, qualitatively or preferably quantitatively, the expression level of the target protein and making a diagnosis of cancer on the basis of this expression level.

In this context, "determining the expression" means qualitative and/or quantitative determinations, of the presence of the target protein of the invention including measuring an amount of biological activity of the target protein in terms of units of activity or units activity per unit time, and so forth.

As used herein, the term "expression" generally refers to the cellular processes by which a polypeptide is produced from RNA.

As used herein, the term "cancer" encompasses cancers in all forms, including polyps, neoplastic cells and preneoplastic cells and includes sarcomas and carcinomas. Exemplary sarcomas and carcinomas include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumour, cervical cancer, testicular tumour, lung carcinoma (including small cell lung carcinoma and non-small cell lung carcinoma), bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma ; leukaemias, e. g., acute lymphocytic leukaemia and acute myelocytic leukaemia (myeloblastic, promyelocytic, myelomonocytic, monocytic and erythroleukaemia); chronic leukaemia (chronic myelocytic (granulocytic) leukaemia and chronic lymphocytic leukaemia); and polycythemia vera, lymphoma (Hodgkin's disease and non-Hodgkin's disease), multiple myeloma, Waldenstrbom's macroglobulinemia, and heavy chain disease.

In a preferred embodiment of the present invention, this method may be applied to diagnosis of colorectal cancer. The terms "colon cancer", "rectal cancer", and "colorectal cancer" are used interchangeably herein.

Species variants are also encompassed by this invention where the patient is a non-human mammal, as are allelic or other variants of the proteins described in Table 2, and any reference to the proteins in that table will be understood to embrace, alleles, homologues or other naturally occurring variants.

Thus included within the definition of the target protein of the invention are amino acid variants of the naturally occurring sequence as provided in any of SEQ ID NOs: 1-11. Preferably, variant sequences are at least 75% homologous to the wild-type sequence, more preferably at least 80% homologous, even more preferably at least 855 homologous, yet more preferably at least 90% homologous or most preferably at least 955 homologous to at least a portion of the reference sequence supplied (SEQ ID NOs: 1-11). In some embodiments the homology will be as high as 94 to 96 or 98%. Homology in this context means sequence similarity or identity, with identity being preferred. To determine whether a candidate peptide region has the requisite percentage similarity or identity to a reference polypeptide or peptide oligomer, the candidate amino acid sequence and the reference amino acid sequence are first aligned using a standard computer programme such as are commercially available and widely used by those skilled in the art. In a preferred embodiment the NCBI BLAST method is used www.ncbi.nlm.nih-.gov/BLAST/). Once the two sequences have been aligned, a percent similarity score may be calculated. In all instances, variants of the naturally-occurring sequence, as detailed in SEQ ID NO: 1-11 herein, must be confirmed for their function as marker proteins. Specifically, their presence or absence in a particular form or in a particular biological compartment must be indicative of the presence or absence of cancer in an individual. This routine experimentation can be carried out by using standard methods known in the art in the light of the disclosure herein.

In one aspect of the present invention, the target protein can be detected using a binding moiety capable of specifically binding the marker protein. By way of example, the binding moiety may comprise a member of a ligand-receptor pair, i.e. a pair of molecules capable of having a specific binding interaction. The binding moiety may comprise, for example, a member of a specific binding pair, such as antibody-antigen, enzyme-substrate, nucleic acid-nucleic acid, protein-nucleic acid, protein-protein, or other specific binding pair known in the art. Binding proteins may be designed which have enhanced affinity for the target protein of the invention. Optionally, the binding moiety may be linked with a detectable label, such as an enzymatic, fluorescent, radioactive, phosphorescent, coloured particle label or spin label. The labelled complex may be detected, for example, visually or with the aid of a spectrophotometer or other detector.

A preferred embodiment of the present invention involves the use of a recognition agent, for example an antibody recognising the target protein of the invention, to contact a sample of tissues, cells, blood or body product, or samples derived therefrom, and screening for a positive response. The positive response may for example be indicated by an agglutination reaction or by a visualisable change such as a colour change or fluorescence, e.g. immunostaining,.or by a quantitative method such as in use of radio-immunological methods or enzyme-linked antibody methods.

The method therefore typically includes the steps of (a) obtaining from a patient a tissue sample to be tested for the presence of cancer cells; (b) producing a prepared sample in a sample preparation process; (c) contacting the prepared sample with a recognition agent, such as an antibody, that reacts with the target protein of the invention; and (d) detecting binding of the recognition agent to the target protein, if present, in the prepared sample. The human tissue sample can be from the colon or any other tissue in which tumour-specific expression of the appropriate protein can be demonstrated. The sample may further comprise sections cut from patient tissues or it may contain whole cells or it may be, for example, a body fluid sample selected from the group consisting of: blood; serum; plasma; fecal matter; urine; vaginal secretion; breast exudate; spinal fluid; saliva; ascitic fluid; peritoneal fluid; sputum; and colorectal exudate, or an effusion, where the sample may contain cells, or may contain shed antigen. A preferred sample preparation process includes tissue fixation and production of a thin section. The thin section can then be subjected to immunohistochemical analysis to detect binding of the recognition agent to the target protein. Preferably, the immunohistochemical analysis includes a conjugated enzyme labelling technique. A preferred thin section preparation method includes formalin fixation and wax embedding. Alternative sample preparation processes include tissue homogenisation. When sample preparation includes tissue homogenisation, a preferred method for detecting binding of the antibody to the target protein is Western blot analysis.

Alternatively, an immunoassay can be used to detect binding of the antibody to the target protein. Examples of immunoassays are antibody capture assays, two-antibody sandwich assays, and antigen capture assays. In a sandwich immunoassay, two antibodies capable of binding the marker protein generally are used, e.g. one immobilised onto a solid support, and one free in solution and labelled with a detectable chemical compound. Examples of chemical labels that may be used for the second antibody include radioisotopes, fluorescent compounds, spin labels, coloured particles such as colloidal gold and coloured latex, and enzymes or other molecules that generate coloured or electrochemically active products when exposed to a reactant or enzyme substrate. When a sample containing the marker protein is placed in this system, the marker protein binds to both the immobilised antibody and the labelled antibody, to form a "sandwich" immune complex on the support's surface. The complexed protein is detected by washing away non-bound sample components and excess labelled antibody, and measuring the amount of labelled antibody complexed to protein on the support's surface. Alternatively, the antibody free in solution, which can be labelled with a chemical moiety, for example, a hapten, may be detected by a third antibody labelled with a detectable moiety which binds the free antibody or, for example, the hapten coupled thereto. Preferably, the immunoassay is a solid support-based immunoassay. Alternatively, the immunoassay may be one of the immunoprecipitation techniques known in the art, such as, for example, a nephelometric immunoassay or a turbidimetric immunoassay. When Western blot analysis or an immunoassay is used, preferably it includes a conjugated enzyme labelling technique.

Although the recognition agent will conveniently be an antibody, other recognition agents are known or may become available, and can be used in the present invention. For example, antigen binding domain fragments of antibodies, such as Fab fragments, can be used. Also, so-called RNA aptamers may be used. Therefore, unless the context specifically indicates otherwise, the term "antibody" as used herein is intended to include other recognition agents. Where antibodies are used, they may be polyclonal or monoclonal. Optionally, the antibody can be produced by a method such that it recognizes a preselected epitope from the target protein of the invention.

The isolated target protein of the invention may be used for the development of diagnostic and other tissue evaluation kits and assays to monitor the level of the proteins in a tissue or fluid sample. For example, the kit may include antibodies or other specific binding moieties which bind specifically to the target protein which permit the presence and/or concentration of the colorectal cancer-associated proteins to be detected and/or quantified in a tissue or fluid sample. Accordingly, the invention further provides for the production of suitable kits for detecting the target protein, which may for example include a receptacle or other means for receiving a sample to be evaluated, and a means for detecting the presence and/or quantity in the sample of the target protein of the invention and optionally instructions for performing such an assay.

In a further aspect of the present invention is provided herein a method of evaluating the effect of a candidate therapeutic drug for the treatment of cancer, said method comprising administering said drug to a patient, removing a cell sample from said patient; and determining the expression profile of the target protein of the invention in said cell sample. This method may further comprise comparing said expression profile to an expression profile of a healthy individual. In a preferred embodiment, said patient is receiving treatment for colorectal cancer and said cell sample is derived from tissues of the colon and/or rectum. In a further preferred embodiment the present invention further provides a method for determine the efficacy of a therapeutic regime at one or more timepoints, said method comprising determining a baseline value for the expression of the protein being tested in a given individual within a given tissue such as a tumour, administering a given therapeutic drug, and then redetermining expression levels of the protein within that given tissue at one or more instances thereafter, observing changes in protein levels as an indication of the efficacy of the therapeutic regime.

In a further aspect of the present invention the target protein of the invention provides a mechanism for the selective targeting of anti-cancer drugs based on metabolism by the target protein within tumours. The present invention therefore provides for the design of, or screening for, drugs that undergo specific metabolism in tumours mediated by the target protein of the invention, whereby this metabolism converts a non-toxic moiety into a toxic one, which kills or inhibits the tumour or makes it more susceptible to other agents. In a further preferred embodiment of the present invention, a method of treating colorectal cancer is provided, said method comprising use of a drug that is specifically metabolised to an active form by contact with the target protein of the invention.

A further aspect of the invention provides for the targeting of cytotoxic drugs or other therapeutic agents, or the targeting of imaging agents, by virtue of their recognition of epitopes derived from the target protein of the invention on the surface of a tumour cell, whether as part of the complete target protein itself or in some degraded form such as in the presentation on the surface of a cell bound to a MHC protein.

A further embodiment of the present invention is the development of therapies for treatment of conditions which are characterized by over-expression of the target protein of the invention via immunotherapeutic approaches. More specifically, the invention provides methods for stimulation of the immune system of cancer patients, for example by activating cytotoxic or helper T-cells which recognise epitopes derived from the protein of the invention so as to implement a cell-mediated or humoral immune response against the tumour. By way of example, the activation of the immune system can be achieved by immunisation with sequences derived from the target protein of the invention in an amount sufficient to provoke or augment an immune response. By way of further example, which is specifically not intended to limit the scope of the invention, these may be administered as naked peptides, as peptides conjugated or encapsulated in one or more additional molecules (e.g. liposomes) such that a pharmacological parameter (e.g. tissue permeability, resistance to endogenous proteolysis, circulating half-life etc) is improved, or in a suitable expression vector which causes the expression of the sequences at an appropriate site within the body to provoke an immune response. The proteins or peptides may be combined with one or more of the known immune adjuvants, such as saponins, GM-CSF, interleukins, and so forth. Peptides that are too small to generate a sufficient immune response when administered alone can be coupled to one or more of the various conjugates used to stimulate such responses which are well known in the art. Furthermore, peptides which form non-covalent complexes with MHC molecules within cells of the host immune system may be used to elicit proliferation of cytolytic T cells against any such complexes in the subject. Such peptides may be administered endogenously or may be administered to isolated T-cells ex-vivo and then reperfused into the subject being treated. Alternatively, the generation of a host immune response can be accomplished by administration of cells, preferably rendered non-proliferative by standard methods, which present relevant T cell or B cell epitopes to trigger the required response.

Because up-regulation of expression of the target protein of the invention is associated with tumour cells, it is likely that these proteins in some way contribute to the process of tumourigenesis or the persistence of tumour cells. Consequently, the present invention provides for the reduction of the expression level of the target protein in tumour cells, for example by the use of suicide inhibitors or by using antisense RNA methods to decrease the synthesis of the protein. Similarly, this reduction in expression levels could also be achieved by down-regulation of the corresponding gene promoter. A preferred method comprises the step of administering to a patient diagnosed as having cancer, such as colorectal cancer, a therapeutically-effective amount of a compound which reduces in vivo the expression of the target protein. In a preferred embodiment, the compound is a polynucleotide, for example, an anti-sense nucleic acid sequence or a peptidyl nucleic acid (PNA), more preferably from 10 to 100 nucleotides in length, capable of binding to and reducing the expression (for example, transcription or translation) of a nucleic acid encoding at least a portion of the target protein of the invention. After administration, the anti-sense nucleic acid sequence or the anti-sense PNA molecule binds to the nucleic acid sequences encoding, at least in part, the target protein thereby to reduce in vivo expression of the target protein. By way of further example, constructs of the present invention capable of reducing expression of the target protein can be administered to the subject either as a naked polynucleotide or formulated with a carrier, such as a liposome, to facilitate incorporation into a cell. Such constructs can also be incorporated into appropriate vaccines, such as in viral vectors (e.g. *vaccinia*), bacterial constructs, such as variants of the well known BCG vaccine, and so forth.

A particularly useful therapeutic embodiment of the present invention provides an oligonucleotide or peptidyl nucleic acid sequence complementary and capable of hybridizing under physiological conditions to part, or all, of the gene encoding the target protein or to part, or all, of the transcript encoding the target protein thereby to reduce or inhibit transcription and/or translation of the target protein gene.

Anti-sense oligonucleotides have been used extensively to inhibit gene expression in normal and abnormal cells. For a recent review, see Phillips, ed., Antisense Technology, in Methods in Enzymology, vols. 313-314, Academic Press; Hartmann, ed., 1999. In addition, the synthesis and use of peptidyl nucleic acids as anti-sense-based therapeutics are described in PCT publications PCT/EP92/01219, PCT/US92/1092, and PCT/US94/013523. Accordingly, the anti-sense-based therapeutics may be used as part of chemotherapy, either alone or in combination with other therapies.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) *Trends Genet.* 15: 358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245).

RNA interference is a two step process. First, dsRNA is cleaved within the cell to yield short interfering RNAs (siRNAs) of about 21-23nt length with 5' terminal phosphate and 3' short overhangs (~2nt) The siRNAs target the corresponding mRNA sequence specifically for destruction (Zamore P. D. Nature Structural Biology, 8, 9, 746-750, (2001)

Thus in one embodiment, the invention provides double stranded RNA comprising a sequence encoding a target protein of the present invention, which may for example be a "long" double stranded RNA (which will be processed to siRNA, e.g., as described above). These RNA products may be synthesised in vitro, e.g., by conventional chemical synthesis methods.

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir S M. et al. Nature, 411, 494-498, (2001)). Thus siRNA duplexes containing between 20 and 25 bps, more preferably between 21 and 23 bps, of the sequence encoding a target protein of the present invention form one aspect of the invention e.g. as produced synthetically, optionally in protected form to prevent degradation. Alternatively siRNA may be produced from a vector, in vitro (for recovery and use) or in vivo.

Accordingly, the vector may comprise a nucleic acid sequence encoding a target protein of the present invention (including a nucleic acid sequence encoding a variant or fragment thereof), suitable for introducing an siRNA into the cell in any of the ways known in the art, for example, as described in any of references cited herein, which references are specifically incorporated herein by reference.

In one embodiment, the vector may comprise a nucleic acid sequence according to the invention in both the sense and antisense orientation, such that when expressed as RNA the sense and antisense sections will associate to form a double stranded RNA. This may for example be a long double stranded RNA (e.g., more than 23nts) which may be processed in the cell to produce siRNAs (see for example Myers (2003) *Nature Biotechnology* 21:324-328).

Alternatively, the double stranded RNA may directly encode the sequences which form the siRNA duplex, as described above. In another embodiment, the sense and antisense sequences are provided on different vectors.

These vectors and RNA products may be useful for example to inhibit de novo production of the protein of the present invention in a cell. They may be used analogously to the expression vectors in the various embodiments of the invention discussed herein.

In particular there is provided double-stranded RNA which comprises an RNA sequence encoding a target protein of the present invention or a fragment thereof, which may be an siRNA duplex consisting of between 20 and 25 bps. Also provided are vectors encoding said dsRNA or siRNA duplexes. Also provided are methods of producing said siRNA duplexes comprising introducing such vectors into a host cell and causing or allowing transcription from the vector in the cell. Separate vectors may encode: (i) the sense sequence of the siRNA duplex, and (ii) the anti-sense sequence of the siRNA duplex.

An additional DNA based therapeutic approach provided by the present invention is the use of a vector which comprises one or more nucleotide sequences, preferably a plurality of these, each of which encodes an immunoreactive peptide derived from the target protein of the invention. Alternatively, a further method of the invention involves combining one or more of these nucleotide sequences encoding peptides derived from the target protein of the invention in combination with nucleotide sequences encoding peptides derived from other tumour markers known in the art to be expressed by cancer cells, and encompasses inclusion of such sequences in all possible variations, such as one from each protein, several from one or more protein and one from each of one or more additional proteins, and so forth.

A further aspect of the present invention provides novel methods for screening for compositions that modulate the expression or biological activity of the target protein of the invention. As used herein, the term "biological activity" means any observable effect resulting from interaction between the target protein and a ligand or binding partner. Representative, but non-limiting, examples of biological activity in the context of the present invention include association of the target protein of the invention with a ligand, such as any of those shown in Table 4.

The term "biological activity" also encompasses both the inhibition and the induction of the expression of the target protein of the invention. Further, the term "biological activity" encompasses any and all effects resulting from the binding of a ligand or other in vivo binding partner by a polypeptide derivative of the protein of the invention. In one embodiment, a method of screening drug candidates comprises providing a cell that expresses the target protein of the invention, adding a candidate therapeutic compound to said cell and determining the effect of said compound on the expression or biological activity of said protein. In a further embodiment, the method of screening candidate therapeutic compounds includes comparing the level of expression or biological activity of the protein in the absence of said candidate therapeutic compound to the level of expression or biological activity in the presence of said candidate therapeutic compound. Where said candidate therapeutic compound is present its concentration may be varied, and said comparison of expression level or biological activity may occur after addition or removal of the candidate therapeutic compound. The expression level or biological activity of said target protein may show an increase or decrease in response to treatment with the candidate therapeutic compound.

Candidate therapeutic molecules of the present invention may include, by way of example, peptides produced by expression of an appropriate nucleic acid sequence in a host cell or using synthetic organic chemistries, or non-peptide small molecules produced using conventional synthetic organic chemistries well known in the art. Screening assays may be automated in order to facilitate the screening of a large number of small molecules at the same time.

As used herein, the terms "candidate therapeutic compound" refers to a substance that is believed to interact with the target protein of the invention (or a fragment thereof), and which can be subsequently evaluated for such an interaction. Representative candidate therapeutic compounds include "xenobiotics", such as drugs and other therapeutic agents, natural products and extracts, carcinogens and environmental pollutants, as well as "endobiotics" such as steroids, fatty acids and prostaglandins. Other examples of candidate compounds that can be investigated using the methods of the present invention include, but are not restricted to, agonists and antagonists of the target protein of the invention, toxins and venoms, viral epitopes, hormones (e. g., opioid peptides, steroids, etc.), hormone receptors, peptides, enzymes, enzyme substrates, co-factors, lectins, sugars, oligonucleotides or nucleic acids, oligosaccharides, proteins, small molecules and monoclonal antibodies.

In one preferred embodiment the present invention provides a method of drug screening utilising eukaryotic or prokaryotic host cells stably transformed with recombinant polynucleotides expressing the target protein of the invention or a fragment thereof, preferably in competitive binding assays. Such cells, either in viable or fixed form, can be used for standard binding assays. For example, the assay may measure the formation of complexes between a target protein and the agent being tested, or examine the degree to which the formation of a complex between the target protein or fragment thereof and a known ligand or binding partner is interfered with by the agent being tested. Thus, the present invention provides methods of screening for drugs comprising contacting such an agent with the target protein of the invention or a fragment thereof or a variant thereof found in a tumour cell and assaying (i) for the presence of a complex between the agent and the target protein, fragment or variant thereof, or (ii) for the presence of a complex between the target protein, fragment or variant and a ligand or binding partner. In such competitive binding assays the target protein or fragment or variant is typically labelled. Free target protein, fragment or variant thereof is separated from that present in a protein: protein complex and the amount of free (i.e. uncomplexed) label is a measure of the binding of the agent being tested to the target protein or its interference with binding of the target protein to a ligand or binding partner, respectively.

Alternatively, an assay of the invention may measure the influence of the agent being tested on a biological activity of the target protein. Thus, the present invention provides methods of screening for drugs comprising contacting such an agent with the target protein of the invention or a fragment thereof or a variant thereof found in a tumour cell and assaying for the influence of such an agent on a biological activity of the target protein, by methods well known in the art. In such activity assays the biological activity of the target protein, fragment or variant thereof is typically monitored by provision of a reporter system. For example, this may involve provision of a natural or synthetic substrate that generates a detectable signal in proportion to the degree to which it is acted upon by the biological activity of the target molecule.

It is contemplated that, once candidate therapeutic compounds have been elucidated, rational drug design methodologies well known in the art may be employed to enhance their efficacy. The goal of rational drug design is to produce structural analogues of biologically active polypeptides of interest or of small molecules with which they interact (e. g. agonists, antagonists, inhibitors) in order to fashion drugs which are, for example, more active or stable forms of the polypeptide, or which, for example, enhance or interfere with the function of a polypeptide in vivo. In one approach, one first determines the three-dimensional structure of a protein of interest, such as the target protein of the invention or, for example, of the target protein in complex with a ligand, by x-ray crystallography, by computer modelling or most typically, by a combination of approaches. For example, the skilled artisan may use a variety of computer programmes which assist in the development of quantitative structure activity relationships (QSAR) that act as a guide in the design of novel, improved candidate therapeutic molecules. Less often, useful information regarding the structure of a polypeptide may be gained by modelling based on the structure of homologous proteins. In addition, peptides can be analysed by alanine scanning (Wells, Methods Enzymol. 202: 390-411, 1991), in which each amino acid residue of the peptide is sequentially replaced by an alanine residue, and its effect on the peptide's activity is determined in order to determine the important regions of the peptide. It is also possible to design drugs based on a pharmacophore derived from the crystal structure of a target-specific antibody selected by a functional assay. It is further possible to avoid the use of protein crystallography by generating anti-idiotypic antibodies to such a functional, target-specific antibody, which have the same three-dimensional conformation as the original target protein. These anti-idiotypic antibodies can subsequently be used to identify and isolate peptides from libraries, which themselves act as pharmacophores for further use in rational drug design.

For use as a medicament in vivo, candidate therapeutic compounds so identified may be combined with a suitable pharmaceutically acceptable carrier, such as physiological saline or one of the many other useful carriers well characterized in the medical art. Such pharmaceutical compositions may be provided directly to malignant cells, for example, by direct injection, or may be provided systemically, provided the formulation chosen permits delivery of the therapeutically effective molecule to tumour cells containing the target protein of the invention. Suitable dose ranges and cell toxicity levels may be assessed using standard dose ranging methodology. Dosages administered may vary depending, for example, on the nature of the malignancy, the age, weight and health of the individual, as well as other factors.

A further aspect of the present invention provides for cells and animals which express the target protein of the invention and can be used as model systems to study and test for substances which have potential as therapeutic agents.

Such cells may be isolated from individuals with mutations, either somatic or germline, in the gene encoding the target protein of the invention, or can be engineered to express or over-express the target protein or a variant thereof, using methods well known in the art. After a test substance is applied to the cells, any relevant trait of the cells can be assessed, including by way of example growth, viability, tumourigenicity in nude mice, invasiveness of cells, and growth factor dependence, assays for each of which traits are known in the art.

Animals for testing candidate therapeutic agents can be selected after mutagenesis of whole animals or after treatment of germline cells or zygotes. As discussed in more detail below, by way of example, such treatments can include insertion of genes encoding the target protein of the invention in wild-type or variant form, typically from a second animal species, as well as insertion of disrupted homologous genes. Alternatively, the endogenous target protein gene(s) of the animals may be disrupted by insertion or deletion mutation or other genetic alterations using conventional techniques that are well known in the art. After test substances have been administered to the animals, the growth of tumours can be assessed. If the test substance prevents or suppresses the growth of tumours, then the test substance is a candidate therapeutic agent for the treatment of those cancers expressing the target protein of the invention, for example of colorectal cancers. These animal models provide an extremely important testing vehicle for potential therapeutic compounds.

Thus the present invention thus provides a transgenic non-human animal, particularly a rodent, which comprises an inactive copy of the gene encoding a target protein of the present invention.

The invention further provides a method of testing a putative therapeutic of the invention which comprises administering said therapeutic to an animal according to the invention and determining the effect of the therapeutic.

For the purposes of the present invention, it will be understood that reference to an inactive copy of the gene encoding a target protein of the present invention includes any non-wild-type variant of the gene which results in knock out or down regulation of the gene, and optionally in a cancer phenotype. Thus the gene may be deleted in its entirety, or mutated such that the animal produces a truncated protein, for example by introduction of a stop codon and optionally upstream coding sequences into the open reading frame of the gene encoding a target protein of the present invention. Equally, the open reading frame may be intact and the inactive copy of the gene provided by mutations in promoter regions.

Generally, inactivation of the gene may be made by targeted homologous recombination. Techniques for this are known as such in the art.

This may be achieved in a variety of ways. A typical strategy is to use targeted homologous recombination to replace, modify or delete the wild-type gene in an embryonic stem (ES) cell. A targeting vector comprising a modified target gene is introduced into ES cells by electroporation, lipofection or microinjection. In a few ES cells, the targeting vector pairs with the cognate chromosomal DNA sequence and transfers the desired mutation carried by the vector into the genome by homologous recombination. Screening or enrichment procedures are used to identify the transfected cells, and a transfected cell is cloned and maintained as a pure population. Next, the altered ES cells are injected into the blastocyst of a preimplantation mouse embryo or alternatively an aggregation chimera is prepared in which the ES cells are placed between two blastocysts which, with the ES cells, merge to form a single chimeric blastocyst. The chimeric blastocyst is surgically transferred into the uterus of a foster mother where the development is allowed to progress to term. The resulting animal will be a chimera of normal and donor cells. Typically the donor cells will be from an animal with a clearly distinguishable phenotype such as skin colour, so that the chimeric progeny is easily identified. The progeny is then bred and its descendants cross-bred, giving rise to heterozygotes and homozygotes for the targeted mutation. The production of transgenic animals is described further by Capecchi, M, R., 1989, Science 244; 1288-1292; Valancius and Smithies, 1991, Mol. Cell. Biol. 11; 1402-1408; and Hasty et al, 1991, Nature 350; 243-246, the disclosures of which are incorporated herein by reference.

Homologous recombination in gene targeting may be used to replace the wild-type gene encoding a target protein of the present invention with a specifically defined mutant form (e.g. truncated or containing one or more substitutions).

The inactive gene may also be one in which its expression may be selectively blocked either permanently or temporarily. Permanent blocking may be achieved by supplying means to delete the gene in response to a signal. An example of such a means is the cre-lox system where phage lox sites are provided at either end of the transgene, or at least between a sufficient portion thereof (e.g. in two exons located either side or one or more introns). Expression of a cre recombinase causes excision and circularisation of the nuclei acid between the two lox sites. Various lines of transgenic animals, particularly mice, are currently available in the art which express cre recombinase in a developmentally or tissue restricted manner, see for example Tsien, Cell, Vol.87(7): 1317-1326, (1996) and Betz, Current Biology, Vol.6(10): 1307-1316 (1996). These animals may be crossed with lox transgenic animals of the invention to examine the function of the gene encoding a target protein of the present invention. An alternative mechanism of control is to supply a promoter from a tetracycline resistance gene, tet, to the control regions of the target gene locus such that addition of tetracycline to a cell binds to the promoter and blocks expression of the gene encoding a target protein of the present invention. Alternatively GAL4, VP16 and other transactivators could be used to modulate gene expression including that of a transgene containing the gene encoding a target protein of the present invention. Furthermore, the target gene could also be expressed in ectopic sites, that is in sites where the gene is not normally expressed in time or space.

Transgenic targeting techniques may also be used to delete the gene encoding a target protein of the present invention. Methods of targeted gene deletion are described by Brenner et al, WO94/21787 (Cell Genesys), the disclosure of which is incorporated herein by reference.

In a further embodiment of the invention, there is provided a non-human animal which expresses the gene encoding a target protein of the present invention at a higher than wild-type level. Preferably this means that the gene encoding a target protein of the present invention is expressed at least 120-200% of the level found in wild-type animals of the same species, when cells which express the gene are compared. Also, this gene could be expressed in an ectopic location where the target gene is not normally expressed in time or space. Comparisons may be conveniently done by northern blotting and quantification of the transcript level. The higher level of expression may be due to the presence of one or more, for example two or three, additional copies of the target gene or by modification to the gene encoding a target protein of the present inventions to provide over-expression, for example by introduction of a strong promoter or enhancer in operable linkage with the wild-type gene. The provision of animals with additional copies of genes may be achieved using the techniques described herein for the provision of "knock-out" animals.

In another aspect, animals are provided in which the gene encoding a target protein of the present invention is expressed at an ectopic location. This means that the gene is expressed in a location or at a time during development which does not occur in a wild-type animal. For example, the gene may be linked to a developmentally regulated promoter such as Wnt-1 and others (Echeland, Y. Et al., Development 120, 2213-2224, 1998; Rinkenberger, J. C. et al., Dev. Genet. 21, 6-10, 1997, or a tissue specific promoter such as HoxB (Machonochie, M. K. et al, Genes & Dev 11, 1885-1895, 1997).

Non-human mammalian animals include non-human primates, rodents, rabbits, sheep, cattle, goats, pigs. Rodents include mice, rats, and guinea pigs. Amphibians include frogs. Fish such as zebra fish, may also be used. Transgenic non-human mammals of the invention may be used for experimental purposes in studying cancer, and in the development of therapies designed to alleviate the symptoms or progression of cancer. By "experimental" it is meant permissible for use in animal experimentation or testing purposes under prevailing legislation applicable to the research facility where such experimentation occurs.

Other features of the invention will be clear to the skilled artisan, and need not be repeated here. The terms and expressions employed herein are used as terms of description and not of limitation; there is no intention in the use of such terms and expressions to exclude any equivalents of the features shown and described or portions thereof, it being recognized that various modifications are possible within the scope of the invention.

The disclosure of all references cited herein, inasmuch as it may be used by those skilled in the art to carry out the invention, is hereby specifically incorporated herein by cross-reference.

Tables and Sequences

Table 1: differentially expressed proteins identified in the present study and already known to be upregulated in colorectal cancer.

Table 2: protein detectable in colorectal cancer samples but not normal colon tissue controls.

Table 3: Clinicopathological characteristics of the cases used for proteome analysis. All the cases were Dukes C colorectal cancers.

Sequence Annex I:

Seq ID No 1: wild-type amino acid sequence of hnRNP-K as sourced from the public SwissProt protein sequence database (SwissProt primary accession number Q07244).

Seq ID No 2: wild-type amino acid sequence of HMG-1 as sourced from the public SwissProt protein sequence database (SwissProt primary accession number P09429).

Seq ID No 3: wild-type amino acid sequence of proteasome subunit alpha type 1 as sourced from the public SwissProt protein sequence database (SwissProt primary accession number P25786).

Seq ID No 4: wild-type amino acid sequence of bifunctional purine biosynthesis protein as sourced from the public SwissProt protein sequence database (SwissProt primary accession number P31939).

Seq ID No 5: wild-type amino acid sequence of STI1 as sourced from the public SwissProt protein sequence database (SwissProt primary accession number P31948).

Seq ID No 6: wild-type amino acid sequence of annexin IV as sourced from the public SwissProt protein sequence database (SwissProt primary accession number P09525).

Seq ID No 7: wild-type amino acid sequence of 60 kDa heat shock protein as sourced from the public SwissProt protein sequence database (SwissProt primary accession number P10809).

Seq ID No 8: wild-type amino acid sequence of T complex protein 1 beta subunit as sourced from the public SwissProt protein sequence database (SwissProt primary accession number P78371).

Seq ID No 9: wild-type amino acid sequence of T complex protein 1 epsilon subunit as sourced from the public SwissProt protein sequence database (SwissProt primary accession number P48643).

Seq ID No 10: wild-type amino acid sequence of mortalin as sourced from the public SwissProt protein sequence database (SwissProt primary accession number P38646).

Seq ID No 11: wild-type amino acid sequence of TER-ATPase as sourced from the public SwissProt protein sequence database (SwissProt primary accession number P55072).

EXAMPLE 1

Identification of Novel Markers

Proteins exhibiting differential expression in clinically resected colorectal tumours and normal colon tissues were identified as follows;

Tissue Samples

Proteomic analysis was performed on fresh frozen tissue samples obtained from primary colorectal cancer resections and which had been stored in the Aberdeen colorectal cancer tissue bank. None of the patients in this study disclosed herein had received chemotherapy or radiotherapy prior to surgery. Representative samples of viable tumour and normal colorectal mucosa (obtained at a distance of at least 5 cm from tumour) were dissected from colorectal cancer excision specimens within 30 minutes of surgical removal, and these dissected samples were immediately frozen in liquid nitrogen and stored at −80° C. prior to analysis. Proteomic analysis was performed in duplicate on 16 matched pairs of frozen tumour and normal colorectal tissue samples. All cases selected were Dukes C colorectal cancers (see Table 3).

Two-Dimensional Gel Electrophoresis

Lysis buffer was prepared according to our established protocols [Lawrie L, Curran S, McLeod H L, Fothergill J E, Murray G I. (2001) Application of laser capture microdissection and proteomics in colon cancer. *Molecular Pathology* 54: 253-258.] and contained urea (42% w/v); thiourea (15% w/v); Chaps [3-(3-cholamidopropyl)dimethylammonio-1-propanesulfonate] (4% w/v); N-decanoyl-N-methylglucamine (Mega 10, 1% w/v), 1-O-Octyl-β-D-glucopyranoside (OBG, 1% w/v), Triton X-100 (polyoxyethylene-p-isooctylphenol) (0.5% v/v); Tris [Tris(hydroxymethyl)aminomethane] (0.5% w/v); DTT (dithiothreitol)(0.8% w/v); IPG 3-10 NL (immobilised pH gradient) buffer (1% v/v), β-mercaptoethanol (1% v/v), tributylphosphine (0.02% v/v). All chemicals were obtained from Amersham Biosciences, UK, with the exception of OBG (Aldrich, UK) and Mega 10 (Sigma, UK).

Frozen sections (10 μm in thickness) of tumour and normal were cut using a cryostat and thirty 10 μm sections of normal tissue and thirty 10 μm sections of tumour tissue were solubilised in 350 μl and 500 μl of lysis buffer respectively [Lawrie L, Curran S, McLeod H L, Fothergill J E, Murray G I. (2001) Application of laser capture microdissection and proteomics in colon cancer. *Molecular Pathology* 54: 253-258]. One section from each sample was stained with haematoxylin and eosin to confirm the diagnosis of each tumour and normal sample; an assessment of tumour cellularity was also made of the tumour sample. 500 μg of normal and tumour sample were loaded, in duplicate, into Immobiline. Dry strip holders and Immobiline Drystrips, pI 3-10 NL, (Amersham Biosciences) were placed into the strip holders. The strips were incubated overnight at room temperature to allow the strips to absorb the samples. After incubation the strips were removed, the strip holders cleaned, and small pieces of dampened electrode strips were then placed over the electrodes in the strip holders to help absorb excess salt during the $1^{st}$ dimension focusing stage. The strips were then placed back into the strip holders and covered with dry strip cover fluid (Amersham Biosciences). The $1^{st}$ dimension focusing was carried out on an IPGPhor system under the following conditions; 30 min at 20V, 1.5 hr at 200V, 1.5 hr gradient to 3500V, 35 hr at 3500V, at 15° C. After completion of focusing the strips were equilibrated for 30 min in equilibration buffer containing urea (36% w/v); 0.5M Tris-HCl, pH 6.9 (20% v/v); 20% SDS (dodecyl sulphate, sodium salt) (20% v/v); DTT (0.4% w/v); glycerol (30% v/v). Strips were equilibrated for a further 30 min in equilibration buffer where DTT was replaced by iodoacetamide (1% w/v). All chemicals were obtained from Amersham Biosciences.

Proteins were separated in the $2^{nd}$ dimension according to their molecular weight on a 7 cm NuPAGE 4-12%, 1 well, Bis-Tris gel (Invitrogen, Paisley, UK). 1st dimension strips were attached to the $2^{nd}$ dimension gel with a 4% low melting point agarose solution (Amersham Biosciences). Normal and tumour samples from the same patient were run in the same gel tank to account for any differences caused by the gel running process. Gels were run at a constant 120V until the bromophenol dye front reached the end of the gel.

Proteins were visualised using a Colloidal Blue Staining Kit (Invitrogen, Paisley, UK). Gels were fixed in a solution containing methanol (50% v/v), acetic acid (10% v/v) for 30 min, then transferred to a staining solution containing methanol (20% v/v), Stainer A (20% v/v), Stainer B (5% v/v) for overnight staining to visualise the proteins. Gels were destained using HPLC-grade water with microwave heating.

Detection of Differential Protein Expression

Destained gels were immediately photographed to produce a black and white image. Gel photographs were scanned to produce a computer image which was then enlarged and printed onto sheets of acetate overlaying the normal and tumour acetate gel pictures allowed proteins which were differentially expressed to be detected. Differentially expressed protein spots were cut from the gel in preparation for identification by mass spectrometry.

Identification of Proteins from Gel

Individual proteins were identified by peptide mass mapping. Protein spots were cut from the gel, washed to remove Coomassie stain, reduced with DTT and alkylated with iodoacetamide then digested with trypsin. Trypsin cleaves proteins (at peptide bonds) after arginine and lysine residues. This action produced a set of tryptic fragments unique to each protein. The resultant tryptic peptides were extracted from the gel pieces under full automation (Pro-Gest Robot, Genomic Solutions). The tryptic fragments were desalted using micro porous tips (Millipore), and deposited onto a sample plate along with a matrix chemical (α-cyano-4-hydroxycinnamic acid) under full automation (Pro-MS, Genomic Solutions). The masses of the tryptic fragments were then determined by Matrix Assisted Laser Desorption Ionisation Time of Flight Mass Spectrometry (MALDI-TOF MS) using a PerSeptive Biosystems Voyager-DE STR mass spectrometer.

To identify the original protein, the masses of the tryptic peptides were entered into the MS-Fit database-searching program. Database-searching programs attempt to match the experimentally obtained masses of tryptic peptides with the theoretically calculated masses of tryptic peptides derived from all proteins within a database. The database search was restricted to search only for human proteins, no restriction was placed on either the molecular weight or the isoelectric point of the protein. To be confident that the correct protein was identified, a clear difference in statistical score between the proteins ranked first and second in the results list had to be obtained.

The study disclosed herein identified as differentially-expressed a number of proteins that have previously been reported as up-regulated in colorectal tumours, thereby validating our experimental methodology and supporting our novel findings. These are shown in Table 1.

Increased expression of both calgranulin A (calcium binding protein S100A8, SwissProt Accession Number P05109) and calgranulin B (calcium binding protein S100A9, SwissProt Accession Number P06702) has been previously reported in colorectal tissues (Stulik J. et al, Electrophoresis 20: 1047-54, 1999). These authors examined 23 matched sets of colorectal carcinoma and normal colon mucosa, and found a significant increase in calgranulin A and B expression in malignant tissues of 70% of donors.

Nucleoside diphosphate kinase A (nm23, SwissProt Accession Number P15531) is widely regarded as a tumour marker in a variety of cancers, but is the subject of some controversy. In certain tumours such as metastatic ovarian carcinoma (Viel et al, Cancer Res 55: 2645-2650, 1995), malignant melanoma (Florenes et al, Cancer Res 52: 6088-91, 1992), hepatocellular carcinoma (Kodera et al, Cancer 73: 259-65, 1994) and prostate cancer (Fishman et al. J Urol. 152: 202-7. 1994) low levels of expression of nm23 correlate with a highly metastatic phenotype, suggesting a role for the protein in inhibiting the process of metastasis. However, among other tumour types, nm23 expression has no apparent relationship to metastatic potential, and may even correlate directly with severity in some of these cancers. For example, a 2-fold increase in nm23 expression is observed in advanced stages of thyroid carcinoma, suggesting a direct correlation of nm23 expression with rapid cell proliferation in thyroid cancer (Zou et al, Br J Cancer 68: 385-8, 1993). Results in colorectal tumours are confusing and contradictory; some researchers report no significant correlation between nm23 expression and colorectal tumour histology, serosal invasion, lymphatic invasion, venous invasion, or lymph node metastasis (Yamaguchi et al, Br J Cancer 68: 1020-4, 1993) whilst others find that nm23 expression increases with local colorectal tumour severity, and reaches even higher levels in liver metastases (Zeng et al, Br J Cancer 70: 1025-30, 1994).

Over-expression of prohibitin (SwissProt Accession Number P35232) has been reported in tumours from a variety of tissue sources, including colon (Coates et al, Exp Cell Res 265: 262-73, 2001) as well as in breast cancer cell lines (Williams et al, Electrophoresis 19: 333-43, 1998).

EXAMPLE 2

Discussion of Novel Markers

TABLE 2 shows 11 novel markers not detectable in normal tissue controls, but found in tumour samples analysed:

Name: hnRNP-K hnRNP-K is a member of the poly(C) binding proteins (PCBPs), which are involved in mRNA stabilization, translational activation, and translational silencing. It binds tightly to poly(C) sequences, and is likely to play a role in the nuclear metabolism of hnRNAs, particularly for pre-mRNAs that contain cytidine-rich sequences. It is known to be upregulated in SV-40 transformed human keratinocytes (Dejgaard et al, J Mol Biol 236: 33-48, 1994), and to be present at higher levels in samples from grade III human breast cancer than in samples from grade II cancer (Mandal et al, J Biol Chem 276: 9699-704, 2001). Over-expression of the related protein hnRNP A2/B1(SwissProt P22626) is associated with tumours, for example in the lung (Mulshine et al, Clin Chest Med. 23: 37-48, 2002) and pancreas (Yan-Sanders et al, Cancer Lett 183: 215-20, 2002), but hnRNP-K has not previously been recognised as a marker of colorectal cancer. U.S. Pat. No. 6,358,683 discloses the elevated expression of hnRNP-K in breast cancer cells and diagnosis of breast cancer from patient blood samples by assaying hnRNP-K amongst other markers.

As shown in Table 2, this protein was not detectable in normal tissue controls, but was found in 14 of the 16 colorectal tumour samples analysed. The amino acid sequence of this protein, identified as hnRNP-K by comparison of the experimentally-derived tryptic peptide fingerprint with entries in the MS-Fit database, is referred to herein as SEQ ID NO:1. hnRNP-K was detected in the tumour of six out of the eight individuals in the good survival cohort compared with all eight of the individuals in the poor survival cohort.

Name: HMG-1

HMG-1 ("HMGB1" in the new nomenclature, also called amphoterin) is a nuclear architectural chromatin-binding factor that bends DNA and promotes protein assembly on specific recognition sequences. However, HMG-1 is also secreted by activated monocytes and macrophages, and is passively released by necrotic or damaged cells into their environment, where it binds with high affinity to RAGE (the receptor for advanced glycation end products) and is a potent mediator of inflammation and immune response. In apoptotic cells generalized underacetylation of histone prevents the release of HMGB1 even after partial autolysis, and thus fail to promote inflammation even if not cleared promptly by phagocytic cells. In this way apoptotic cells are prevented from generating the signal that is broadcast by cells damaged or killed by trauma (Scaffidi et al, Nature 418: 191-5, 2002). Overexpression of HMGB1 induced by steroid hormones protects chromatin/platin adducts from the nuclear DNA repair apparatus (He et al; PNAS 97: 5768-72, 2000). HMGB1 is found in many cell types and described as a ubiquitous nuclear protein present at a copy number of ~$10^6$ per typical mammalian cell, but its expression may be associated with a dividing, DNA-replicating phenotype. As the study disclosed herein involves an enrichment of patient samples for cytoplasmic proteins we might expect not to see HMGB1 in normal samples, and it may be that in tumour cells HMGB1 is released from nuclear sequestration and is detected by proteomic examination of the cytoplasm. The related HMGA proteins (e.g. HMGI(Y)) are known tumour antigens; HMGI(Y) protein has been shown to be overexpressed in various human malignancies, including colon, prostate and thyroid carcinomas (Chiappetta et al, Int. J. Can 91: 147-51, 2001). HMGB1 has not previously been reported as a tumour antigen, and its use in diagnosis of cancers is not described in the patent literature. Modulation of HMG1's interaction with the RAGE receptor, which is known to stimulate cell mobility and replication and to trigger inflammatory responses, is the subject of several patent applications (e.g. WO 0047104, WO 02070473, WO 02069965, WO 0192210).

As shown in Table 2, this protein was not detectable in normal tissue controls, but was found in 14 of the 16 colorectal tumour samples analysed. The amino acid sequence of this protein, identified as HMG-1 by comparison of the experimentally-derived tryptic peptide fingerprint with entries in the MS-Fit database, is referred to herein as SEQ ID NO:2. HMG-1 was detected in the tumours of seven of the eight individuals in each of the good survival and poor survival cohorts.

Name: Proteasome Subunit Alpha Type 1

Proteasome subunit alpha type 1 (also "proteasome component C2") is a component of the 26S proteasome, a large multicatalytic protease complex (reviewed by Naujokat & Hoffmann, Lab Invest 82: 965-80, 2002, and Coux, Prog Mol Subcell Biol. 29: 85-107, 2002). This complex, which is found in the cytoplasm and nucleus of all eukaryotic cells, is the terminal step in the ubiquitin-protease mechanism, which regulates basic cellular processes through targeted degradation of regulatory proteins such as those governing the cell cycle. The 26S proteasome complex is composed of the barrel-shaped 20S catalytic core unit capped at each end by the 19S regulatory complex. The non-catalytic alpha subunits form the outer surface of the 26S barrel, and mediate substrate translocation into the central cavity and interaction between the 20S and 19S subunits. Whilst derangement of proteasome function is a known feature of certain diseases, including cancer and neurodegenerative conditions, and inhibition of proteasome function is a therapeutic goal of cancer research (see for example Shah et al, Surgery 131: 595-600, 2002), up-regulation of expression of subunit alpha type 1 has not previously been observed in cancer. US5843715 teaches the use of genetically-engineered variant proteasome subunits to direct antigen processing and presentation towards desired antigens (e.g. tumour antigens, Alzheimer's proteins etc) for therapeutic benefit.

As shown in Table 2, this protein was not detectable in normal tissue controls, but was found in 13 of the 16 colorectal tumour samples analysed. The amino acid sequence of this protein, identified as proteasome subunit alpha type 1 by comparison of the experimentally-derived tryptic peptide fingerprint with entries in the MS-Fit database, is referred to herein as SEQ ID NO:3. Proteasome subunit alpha type 1 was detected in the tumours of six of the eight individuals in the good survival cohort and seven of the eight individuals in the poor survival cohort.

Name: Bifunctional Purine Biosynthesis Protein

The human purH gene encodes this 591-amino acid bifunctional protein which exhibits the final two activities of the purine nucleotide biosynthetic pathway, AICARFT and IMPCH, located within the C-terminal and N-terminal regions, respectively (Rayl et al., J Biol Chem 271: 2225-33, 1996; Sugita et al, J Biochem (Tokyo) 122: 309-13 1997). As with another enzymatic activity earlier in the pathway, glycinamide ribonucleotide formyltransferase (GARFT), it requires a reduced folate cofactor, 10-formyltetrahydrofolate. AICARFT inhibition is thought to be the origin of the anti-purine effects of anti-folates such as methotrexate whose primary target is dihydrofolate reductase (Budzik et al, Life Sci 66: 2297-307, 2000). Due to the central role played by this pathway in the synthesis of nucleotides for DNA replication, its component enzymes are of interest as targets for chemotherapy (see for example Greasley et al, Nat Struct Biol 8: 402-6). Inhibitors of GARFT are currently in clinical trials as anti-neoplastic agents (e.g. Tularik Inc.'s T64/lometrexol, Eli Lilly's LY309887, Agouron Pharmaceuticals' AG2037). WO0056924 discloses an association between biallelic markers of a PURH gene and cancer, particularly prostate cancer, and provides means to determine the predisposition of individuals to cancer as well as means for the diagnosis of cancer and for the prognosis/detection of an eventual treatment response to agents acting on cancer. WO9413295 and WO0013688 disclose inhibitors of GARFT and AICARFT, and their use as antiproliferative agents.

As shown in Table 2, this protein was not detectable in normal tissue controls, but was found in 12 of the 16 colorectal tumour samples analysed. The amino acid sequence of this protein, identified as bifunctional purine biosynthesis protein by comparison of the experimentally-derived tryptic peptide fingerprint with entries in the MS-Fit database, is referred to herein as SEQ ID NO:4. Bifunctional purine biosynthesis protein was detected in the tumours of five of the eight individuals in the good survival cohort compared with seven of the eight individuals in the poor survival cohort.

Name: STI-1

The molecular chaperone Hsp90 plays an essential role in the folding and activation of a set of client proteins involved in cell cycle regulation, signal transduction, and responsiveness to steroid hormone, in a manner dependent on its own endogenous ATPase activity (reviewed by Pearl & Prodromou, Curr Opin Struct Biol 10: 46-51, 2000). From experiments in yeast it is known that for some client proteins the co-chaperone stress-inducible protein 1 (STI1, also called Hsp70/Hsp90 organizing protein (Hop) or p60) acts as a scaffold for assembly of the Hsp70/Hsp90 chaperone heterocomplex, recruiting Hsp70 and the bound client to Hsp90 and sterically inhibiting Hsp90 ATPase activity during assembly (Johnson et al, J Biol Chem 273: 3679-86, 1998; Richter et al, J Biol Chem. Jan. 13, 2003 [e-publication ahead of print]). The phosphorylation of murine STI1 by casein kinase II (CKII) at S189 and by cdc2 kinase (p34cdc2) at T198 has been implicated as a potential cell cycle checkpoint (Longshaw et al, Biol Chem 381: 1133-8, 2000). STI1 has also been observed to bind TCP-1, subunits beta and epsilon of which were also identified as cancer markers in the present study, stimulating its nucleotide exchange activity (Gebauer et al, J Biol Chem 273: 29475-80, 1998).

As shown in Table 2, this protein was not detectable in normal tissue controls, but was found in 12 of the 16 colorectal tumour samples analysed. The amino acid sequence of this protein, identified as STI1 by comparison of the experimentally-derived tryptic peptide fingerprint with entries in the MS-Fit database, is referred to herein as SEQ ID NO:5. STI1 was detected in the tumours of five of the eight individuals in the good survival cohort and seven of the eight individuals in the poor survival cohort.

Name: Annexin IV

Annexin IV (also called annexin A4) is a member of the annexin family of Ca2+- and phospholipid-binding proteins, which have poorly defined functions in membrane-related events along exocytotic and endocytotic pathways. Annexin IV is threonine phosphorylated by protein kinase C (Kaetzel et al, Biochemistry 40: 4192-9, 2001), binds to surfactant protein A in a $Ca^{2+}$-dependent manner (Sohma et al, Biochem. J. 312: 175-81, 1995) and may bind to glycosylphosphatidylinositol-anchored glycoprotein GP-2, a major component of the zymogen granule membrane (Tsujii-Hayashi et al, J Biol Chem 277: 47493-9, 2002). IHC analysis in a broad variety of human tissues indicates that annexin IV is almost exclusively found in epithelial cells (Dreier et al, Histochem Cell Biol 110: 137-48, 1998). The over-expression of annexin IV in C6 cells by transfection with annexin IV-DNA induces activation of NFkappaB (Ohkawa et al, Biochim Biophys Acta 1588: 217, 2002), while the Fas-induced cell death of Jurkat T-lymphocytes is accompanied by translocation of annexin IV from the nucleus to the cytosol (Gerner et al, J Biol Chem 275: 39018-26, 2000). The protein also plays a role in the paclitaxel resistant phenotype of the H460/T800 cell line and is among the earliest proteins induced in cells in response to cytotoxic stress such as antimitotic drug treatment (Han et al, Br J Cancer 83: 83-8, 2000). Elevated levels of annexin IV have been demonstrated by specific double-antibody radioimmunoassay in the sera of 47.3% (35 of 74) cervical cancer patients and 41.9% (18 of 43) endometrial cancer patients (Gocze et al, Strahlenther Onkol 167: 538-44, 1991). The related protein annexin II appears to be overexpressed in advanced colorectal carcinoma and may be related to the progression and metastatic spread of the disease (Emoto et al, Cancer 92: 1419-26, 2001) but annexin IV has not previously been identified as a marker of colorectal tumours. WO0111372 discusses the diagnosis of cancers by means of detecting increased expression of annexin proteins in biological samples, but provides examples of annexins I and II only, whilst WO0012547 discusses use of annexin V as a marker in the diagnosis of cancer. U.S. Pat. No. 5,316,915 describes the production of an antibody capture assay to detect antibodies against annexins (including annexin IV) within human body fluids.

As shown in Table 2, this protein was not detectable in normal tissue controls, but was found in 11 of the 15 colorectal tumour samples analysed. The amino acid sequence of this protein, identified as annexin IV by comparison of the experimentally-derived tryptic peptide fingerprint with entries in the MS-Fit database, is referred to herein as SEQ ID NO:6. Annexin IV was detected in the tumours of four of the eight individuals in the good survival cohort compared with seven of the seven individuals in the poor survival cohort, showing that this particular protein constitutes a useful prognostic indicator in certain cancers such as colorectal carcinoma.

Name: 60 kDa Heat Shock Protein 60 kDa heat shock protein (hsp60) is abundant in a variety of mammalian cells under normal conditions (Welch et al, Physiol. Rev. 72: 1063-81, 1992), where its major functions are protein chaperoning and protein folding (reviewed by Bukau & Horwich, Cell 92: 351-66, 1998). Both processes are co-regulated by hsp10. hsp60 has been shown to bind a diverse range of cellular protein components; recently identified binding partners include the calcineurin B regulatory subunit of the $Ca^{2+}$/calmodulin-dependent protein phosphatase calcineurin (Li & Handschumacher, Biochim Biophys Acta 1599: 72-81, 2002), the human hepatitis B virus polymerase (Park & Jung, J. Virol. 75: 6962-8, 2001), integrin alpha 3 beta 1 (Barazi et al, Cancer Res 62: 1541-8, 2002), the infectious prion protein PrP (Stockel & Hartl, J Mol Biol 313: 861-7, 2001) and a receptor molecule on macrophages found to be distinct from receptors for other members of the heat shock protein family (Habich et al, J Immunol 168: 569-76, 2002). Whereas aberrant expression of hsp60 has been associated with autoimmune disease, hsp6o has a role together with hsp7o in antigen presentation in malignant diseases (Multhoff et al, Int. J. Cancer 61: 272-279, 1995), with enhanced hsp60 expression reported in myeloid leukaemia (Chant et al, Br. J. Haematol., 90: 163-8, 1995), breast carcinoma (Franzen et al, Electrophoresis, 18: 582-7, 1997; Bini et al, Electrophoresis 18: 2832-41, 1997) and prostate cancers (Cornford et al, Cancer Res 60: 7099-105, 2000). Two proteins of 40 kDa and 47 kDa have been detected in colorectal tumours and not in normal tissue via immunoblotting with an antibody to hsp60(Otaka et al, J Clin Gastroenterol 21: 224-9, 1995), but up-regulation of hsp60 expression in colorectal tumours has not previously been definitively observed. U.S. Pat. No. 5,434,046 discusses prognosis of ovarian cancer treated with cis-platin by measurement of Hsp60 expression.

As shown in Table 2, this protein was not detectable in normal tissue controls, but was found in 11 of the 16 colorectal tumour samples analysed. The amino acid sequence of this protein, identified as 60 kDa heat shock protein by comparison of the experimentally-derived tryptic peptide fingerprint with entries in the MS-Fit database, is referred to herein as SEQ ID NO:7. 60 kDa heat shock protein was detected in the tumours of four of the eight individuals in the good survival cohort compared with seven of the eight individuals in the poor survival cohort, showing that this particular protein constitutes a useful prognostic indicator in certain cancers such as colorectal carcinoma.

Name: T Complex Protein 1 Beta Subunit

The TCP-1 ring complex (TRiC; also called CCT, for chaperonin containing TCP-1) is a large (approximately 900 kDa) ring-shaped multisubunit complex consisting of eight different, yet homologous, subunits ranging between 50 and 60 kDa, which include the TCP-1 beta species (Frydman et al, EMBO J. 11: 4767-78, 1992; Gao et al, Cell 69:1043-50, 1992; Lewis et al, Nature 358: 249-252, 1992). TCP-1 mediates protein folding of an as yet poorly defined physiological substrate spectrum in the eukaryotic cytosol, binding client proteins within its central cavity and inducing their folding by an ATP-dependent mechanism. Genetic and biochemical data show that it is required for the folding of the cytoskeletal proteins actin and tubulin, and TCP-1 was originally proposed to be a chaperone specialized for the folding of these proteins (Lewis et al, J. Cell Biol. 132: 1-4, 1996). However, recent experiments suggest a broader substrate spectrum of distinct proteins that require TCP-1 for proper folding in vivo, including the Von Hippel-Lindau tumour suppressor protein and cyclin E (Dunn et al, J Struct Biol 135: 176-84, 2001). Analysis of auto-antibodies in sera from astrocytoma patients identified TCP-1 as a potential preferentially-expressed antigen in such tumours (Schmits R et al, Int J Cancer 98: 73-7, 2002), and expression of the TCP-1 subunit has been linked with the S to G2/M phase transition of the cell cycle (Dittmar et al, Cell Biol Int 21: 383-91, 1997).

As shown in Table 2, this protein was not detectable in normal tissue controls, but was found in 11 of the 16 colorectal tumour samples analysed. The amino acid sequence of this protein, identified as T complex protein 1 beta subunit by comparison of the experimentally-derived tryptic peptide fingerprint with entries in the MS-Fit database, is referred to herein as SEQ ID NO:8. T complex protein 1 beta subunit was detected in the tumours of five of the eight individuals in the good survival cohort and six of the eight individuals in the poor survival cohort.

Name: T Complex Protein 1 Epsilon Subunit

The TCP-1 ring complex (TRiC; also called CCT, for chaperonin containing TCP-1) is a large (approximately 900 kDa) ring-shaped multisubunit complex consisting of eight different, yet homologous, subunits ranging between 50 and 60 kDa, which include the TCP-1 epsilon species (Frydman et al, EMBO J. 11: 4767-78, 1992; Gao et al, Cell 69:1043-50, 1992; Lewis et al, Nature 358: 249-252, 1992). TCP-1 mediates protein folding of an as yet poorly defined physiological substrate spectrum in the eukaryotic cytosol, binding client proteins within its central cavity and inducing their folding by an ATP-dependent mechanism. Genetic and biochemical data show that it is required for the folding of the cytoskeletal proteins actin and tubulin, and TCP-1 was originally proposed to be a chaperone specialized for the folding of these proteins (Lewis et al, J. Cell Biol. 132: 1-4, 1996). However, recent experiments suggest a broader substrate spectrum of distinct proteins that require TCP-1 for proper folding in vivo, including the Von Hippel-Lindau tumour suppressor protein and cyclin E (Dunn et al, J Struct Biol 135: 176-84, 2001). Epstein-Barr virus-encoded nuclear protein EBNA-3 is known to interact with the TCP-1 epsilon-subunit (Kashuba et al, J Hum Virol. 2: 33-7, 1999). Analysis of auto-antibodies in sera from astrocytoma patients identified TCP-1 as a potential preferentially-expressed antigen in such tumours (Schmits R et al, Int J Cancer 98: 73-7, 2002), and expression of the TCP-1 subunit has been linked with the S to G2/M phase transition of the cell cycle (Dittmar et al, Cell Biol Int 21: 383-91, 1997).

As shown in Table 2, this protein was not detectable in normal tissue controls, but was found in 11 of the 16 colorectal tumour samples analysed. The amino acid sequence of this protein, identified as T complex protein 1 epsilon subunit by comparison of the experimentally-derived tryptic peptide fingerprint with entries in the MS-Fit database, is referred to herein as SEQ ID NO:9. T complex protein 1 epsilon subunit was detected in the tumour of only four of the eight individuals in the good survival cohort compared with seven of the eight individuals in the poor survival cohort, showing that this particular protein constitutes a useful prognostic indicator in certain cancers such as colorectal carcinoma.

Name: Mortalin

Human mortalin (also called stress-70 protein) is a member of the hsp 70 family of proteins initially identified by virtue of its association with a cellular mortal phenotype. The subcellular localisation of mortalin is distinct in normal and immortalised cells, with cytosolic and perinuclear distribution patterns distinguishing the mortal phenotype from the immortal, respectively. Consistently, the cytosolic mortalin is seen to have a senescence-inducing function in contrast to the perinuclear mortalin which has no detectable effect on cellular phenotype (Wadhwa et al, Histol Histopathol 17: 1173-7, 2002; Kaul et al, Exp Gerontol 37: 1157-64, 2002). The human mortalin gene, HSPA9, has been localized to chromosome 5, band q31, a region that is frequently deleted in myeloid leukaemias and myelodysplasia, making it a candidate tumour suppressor gene, and has presumed functions in the stress response, intracellular trafficking, antigen processing, control of cell proliferation, differentiation and tumourigenesis. Transfection of murine 3T3 cells with human mortalin cDNA results in their malignant transformation (Wadhwa et al, J Biol Chem 268: 6615-21, 1993), as does transfection with the murine homologue mot-2 (Kaul et al, Oncogene 17: 907-11, 1998), which is known to bind and inactivate the tumour suppressor protein p53 (Wadhwa et al, J. Biol. Chem 273: 29586-91, 1998). A number of binding partners for mortalin have confirmed, including glucose regulated protein 94 (Takano et al, Biochem J. 357: 393-8, 2001), fibroblast growth factor 1 (Mizukoshi et al, Biochem J. 343: 461-6, 1999) and the interleukin 1 receptor type 1 (Sacht et al, Biofactors 9: 49-60, 1999). Proteomic analysis of human breast ductal carcinoma and histologically normal tissue has identified mortalin as highly expressed in all carcinoma specimens, and less intense and occasionally undetectable in normal tissue (Bini et al, Electrophoresis 18: 2832-41, 1997). Mortalin expression is also elevated in a variety of neurological tumours, including low-grade astrocytoma, anaplastic astrocytoma, glioblastoma, meningiomas, neurinomas, pituitary adenomas, and metastases thereof (Takano et al, Exp Cell Res 237: 38-45, 1997). WO0144807 describes a screening system for drugs that disrupt interaction of p53 with mortalin. U.S. Pat. No. 5,627,0394 discusses characterisation of intracellular mortalin expression with an anti-mortalin antibody and comparison with the "complementation group" of immortalised cells, which is described as an indicator of cellular mortality/immortality phenotype.

As shown in Table 2, this protein was not detectable in normal tissue controls, but was found in 9 of the 16 colorectal tumour samples analysed. The amino acid sequence of this protein, identified as mortalin by comparison of the experimentally-derived tryptic peptide fingerprint with entries in the MS-Fit database, is referred to herein as SEQ ID NO:10. Mortalin was detected in the tumour of only three of the eight individuals in the good survival cohort compared with six of the eight individuals in the poor survival cohort, showing that this particular protein constitutes a useful prognostic indicator in certain cancers such as colorectal carcinoma.

Name: TER-ATPase

TER ATPase, also called valosin-containing protein (VCP), is the mammalian homologue of the Saccharomyces cerevisiae cell cycle control protein cdc48p (reviewed by Wojcik, Trends Cell Biol 12: 212, 2002). It is a homohexameric protein exhibiting a nuclear and cytoplasmic distribution, which has multiple biological functions and has been shown in murine cells to be tyrosine phosphorylated in response to T cell antigen receptor activation, which may provide a link between TCR ligand binding and cell cycle control (Egerton et al, EMBO J 11: 3533-40, 1992). TER ATPase acts as a chaperone in membrane fusions involved in the transfer of transition vesicles from the transitional endoplasmic reticulum to the Golgi apparatus. It also physically targets ubiquitinated nuclear factor kappaB inhibitor to the proteasome for degradation (Dai et al, J Biol Chem 273: 3562-73, 1998). Loss of TER ATPase function results in an inhibition of Ub-Pr-mediated degradation and an accumulation of ubiquitinated proteins, suggesting a role in the degradation of multiple Ub-Pr pathway substrates (Dai & Li, Nat Cell Biol 3: 740-4, 2001). TER ATPase is reported to bind residues 303-625 of the BRCA1 protein via its N-terminal region, and may thereby participate as an ATP transporter in DNA damage-repair functions (Zhang et al, DNA Cell Biol 19: 253-63, 2000). Stimulation of TER ATPase-transfected Dunn cells (a murine osteosarcoma cell line) with TNFalpha induced persistent activation of NFkappaB via enhanced cytoplasmic degradation of p-IkappaBalpha, a reduced rate of apoptosis and increased metastatic potential when used to inoculate male C3H mice (Asai et al, Jpn J Cancer Res 93: 296-304, 2002). Hepatocellular carcinoma (HCC) patients who had more TER ATPase in their tumours than in normal endothelial tissue showed a higher rate of portal vein invasion in the tumour and poorer disease-free and overall survival than patients in whose tumour cells the staining intensity was weaker than in normal tissue, making TER ATPase a prognostic indicator in patients with HCC (Yamamoto et al, J Clin Oncol 21: 447-52, 2003). W00216938 discusses a method of screening for compounds that treat neurodegenerative diseases by inhibiting binding of TER ATPase to an abnormal protein substrate.

As shown in Table 2, this protein was not detectable in normal tissue controls, but was found in 7 of the 16 colorectal tumour samples analysed. The amino acid sequence of this protein, identified as TER ATPase by comparison of the experimentally-derived tryptic peptide fingerprint with entries in the MS-Fit database, is referred to herein as SEQ ID NO:11. TER ATPase was detected in the tumour of only one of the eight individuals in the good survival cohort compared with six of the eight individuals in the poor survival cohort, showing that this particular protein constitutes a useful prognostic indicator in certain cancers such as colorectal carcinoma.

TABLE 1

Differentially expressed proteins identified in the present study and already known to be upregulated in colorectal cancer

| Abbreviated name | SwissProt Accession No. | full name | frequency of up-regulation |
|---|---|---|---|
| calgranulin A | P05109 | S100 calcium binding protein A8 | 10/13 (77%) |
| calgranulin B | P06702 | S100 calcium binding protein A9 | 12/16 (75%) |
| nm-23 | P15531 | nucleoside diphosphate kinase A | 12/16 (75%) |
| — | P35232 | prohibitin | 9/16 (56%) |

TABLE 2

Proteins detectable in colorectal cancer samples but not normal colon tissue controls: novel findings of the present study

| Abbreviated name | SwissProt Accession No. | full name | frequency of up-regulation |
|---|---|---|---|
| hnRNP K | Q07244 | heterogeneous nuclear riboprotein K | 14/16 (88%) |
| HMGB1 | P09429 | high mobility group protein 1 (amphoterin) | 14/16 (88%) |
| — | P25786 | proteasome subunit alpha type 1 | 13/16 (81%) |
| PURH | P31939 | bifunctional purine biosynthesis protein | 12/16 (75%) |
| STI1 | P31948 | stress-induced phosphoprotein 1 | 12/16 (75%) |
| — | P09525 | annexin IV (annexin A4) | 11/15 (73%) |
| Hsp60 | P10809 | 60 kDa heat shock protein | 11/16 (69%) |
| TCP-Iβ | P78371 | T-complex protein 1, beta subunit | 11/16 (69%) |
| TCP-1ε | P48643 | T-complex protein 1, epsilon subunit | 11/69 (69%) |
| mortalin | P38646 | mitochondrial stress-70 protein | 9/16 (56%) |
| TER ATPase | P55072 | transitional endoplasmic reticulum ATPase | 7/16 (44%) |

TABLE 3

Clinicopathological characteristics of the cases used for proteome analysis. All the cases were Dukes C colorectal cancers.

| characteristics | | |
|---|---|---|
| Sex | Male: | n = 8 |
| | Female: | n = 8 |
| Age | <55 years: | n = 6 |
| | ≧55 years: | n = 10 |
| Site | Proximal: | n = 8 |
| | Distal: | n = 8 |
| Tumour differentiation | Well: | n = 0 |
| | Moderate: | n = 15 |
| | Poor: | n = 1 |

TABLE 4

| full name | example ligands |
|---|---|
| heterogeneous nuclear riboprotein K | cytidine-rich polyribonucleotides |
| high mobility group protein 1 (amphoterin) | Chromatin |
| proteasome subunit alpha type 1 | other components of the 26S proteasome, including the 20S and 19S subunits |
| bifunctional purine biosynthesis protein | the purine synthesis intermediates AICAR (aminoimidazole carboxamide ribonucleotide) and FAICAR (formylaminoimidazole carboxamide ribonucleotide) |
| stress-induced phosphoprotein 1 | 70 kDa heat shock protein, 90 kDa heat shock protein, case in kinase II, cdc2 kinase or T complex protein 1 |
| annexin IV (annexin A4) | protein kinase C, surfactant protein A or glycosylphosphatidylinositol-anchored glycoprotein GP-2. |
| 60 kDa heat shock protein | calcineurin B, the human hepatitis B virus polymerase, integrin alpha 3 beta 1 or the infectious prion protein PrP |
| T-complex protein 1, beta subunit | actin, tubulin, the Von Hippel-Lindau tumour suppressor protein or cyclin E |
| T-complex protein 1, epsilon subunit | actin, tubulin, the Von Hippel-Lindau tumour suppressor protein, cyclin E or the Epstein-Barr virus-encoded nuclear protein EBNA-3 |
| mitochondrial stress-70 protein | Glucose regulated protein 94, fibroblast growth factor 1 or the interleukin 1 receptor type 1 |
| transitional endoplasmic reticulum ATPase | nuclear factor kappa B inhibitor |

```
SEQ ID NO:1 - hnRNP-K
METEQPEETF PNTETNGEFG KRPAEDMEEE QAFKRSRNTD EMVELRILLQ SKNAGAVIGK
GGKNIKALRT DYNASVSVPD SSGPERILSI SADIETIGEI LKKIIPTLEE GLQLPSPTAT
SQLPLESDAV ECLNYQHYKG SDFDCELRLL IHQSLAGGII GVKGAKIKEL RENTQTTIKL
FQECCPHSTD RVVLIGGKPD RVVECIKIIL DLISESPIKG RAQPYDPNFY DETYDYGGFT
MMFDDRRGRP VGFPMRGRGG FDRMPPGRGG RPMPPSRRDY DDMSPRRGPP PPPPGRGGRG
GSRARNLPLP PPPPPRGGDL MAYDRRGRPG DRYDGMVGFS ADETWDSAID TWSPSEWQMA
```

-continued

```
YEPQGGSGYD YSYAGGRGSY GDLGGPIITT QVTIPKDLAG SIIGKGGQRI KQIRHESGAS
IKIDEPLEGS EDRIITITGT QDQIQNAQYL LQNSVKQYSG KFF

SEQ ID NO:2 - HMG-1
GKGDPKKPRG KMSSYAFFVQ TCREEHKKKH PDASVNFSEF SKKCSERWKT MSAKEKGKFE
DMAKADKARY EREMKTYIPP KGETKKKFKD PNAPKRPPSA FFLFCSEYRP KIKGEHPGLS
IGDVAKKLGE MWNNTAADDK QPYEKKAAKL KEKYEKDIAA YRAKGKPDAA KKGVVKAEKS
KKKKEEEEDE DEEEDEEEEE DEEDEDEEED DDDE

SEQ ID NO:3 - proteasome subunit alpha type 1
MFRNQYDNDV TVWSPQGRIH QIEYAMEAVK QGSATVGLKS KTHAVLVALK RAQSELAAHQ
KKILHVDNHI GISIAGLTAD ARLLCNFMRQ ECLDSRFVFD RPLPVSRLVS LIGSKTQIPT
QRYGRRPYGV GLLIAGYDDM GPHIFQTCPS ANYFDCRAMS IGARSQSART YLERHMSEFM
ECNLNELVKH GLRALRETLP AEQDLTTKNV SIGIVGKDLE FTIYDDDDVS PFLEGLEERP
QRKAQPAQPA DEPAEKADEP MEH SEQ ID NO:4 - bifunctional purine biosynthesis protein
MAPGQLALFS VSDKTGLVEF ARNLTALGLN LVASGGTAKA LRDAGLAVRD VSELTGFPEM
LGGRVKTLHP AVHAGILARN IPEDNADMAR LDFNLIRVVA CNLYPFVKTV ASPGVTVEEA
VEQIDIGGVT LLRAAAKNHA RVTVVCEPED YVVVSTEMQS SESKDTSLET RRQLALKAFT
HTAQYDEAIS DYFRKQYSKG VSQMPLRYGM NPHQTPAQLY TLQPKLPITV LNGAPGFINL
CDALNAWQLV KELKEALGIP AAASFKHVSP AGAAVGIPLS EDEAKVCMVY DLYKTLTPIS
AAYARARGAD RMSSFGDFVA LSDVCDVPTA KIISREVSDG IIAPGYEEEA LTILSKKKNG
NYCVLQMDQS YKPDENEVRT LFGLHLSQKR NNGVVDKSLF SNVVTKNKDL PESALRDLIV
ATIAVKYTQS NSVCYAKNGQ VIGIGAGQQS RIHCTRLAGD KANYWWLRHH PQVLSMKFKT
GVKRAEISNA IDQYVTGTIG EDEDLIKWKA LFEEVPELLT EAEKKEWVEK LTEVSISSDA
FFPFRDNVDR AKRSGVAYIA APSGSAADKV VIEACDELGI ILAHTNLRLF HH SEQ ID NO:5 - STI1
MEQVNELKEK GNKALSVGNI DDALQCYSEA IKLDPHNHVL YSNRSAAYAK KGDYQKAYED
GCKTVDLKPD WGKGYSRKAA ALEFLNRFEE AKRTYEEGLK HEANNPQLKE GLQNMEARLA
ERKFMNPFNM PNLYQKLESD PRTRTLLSDP TYRELIEQLR NKPSDLGTKL QDPRIMTTLS
VLLGVDLGSM DEEEEIATPP PPPPPKKETK PEPMEEDLPE NKKQALKEKE LGNDAYKKKD
FDTALKHYDK AKELDPTNMT YITNQAAVYF EKGDYNKCRE LCEKAIEVGR ENREDYRQIA
KAYARIGNSY FKEEKYKDAI HFYNKSLAEH RTPDVLKKCQ QAEKILKEQE RLAYINPDLA
LEEKNKGNEC FQKGDYPQAM KHYTEAIKRN PKDAKLYSNR AACYTKLLEF QLALKDCEEC
IQLEPTFIKG YTRKAAALEA MKDYTKAMDV YQKALDLDSS CKEAADGYQR CMMAQYNRHD
SPEDVKRRAM ADPEVQQIMS DPAMRLILEQ MQKDPQALSE HLKNPVIAQK IQKLMDVGLI
AIR SEQ ID NO:6 - annexin IV
ATKGGTVKAA SGFNAMEDAQ TLRKAMKGLG TDEDAIISVL AYRNTAQRQE IRTAYKSTIG
RDLIDDLKSE LSGNFEQVIV GMMTPTVLYD VQELRRAMKG AGTDEGCLIE ILASRTPEEI
RRISQTYQQQ YGRSLEDDIR SDTSFMFQRV LVSLSAGGRD EGNYLDDALV RQDAQDLYEA
GEKKWGTDEV KFLTVLCSRN RNHLLHVFDE YKRISQKDIE QSIKSETSGS FEDALLAIVK
CMRNKSAYFA EKLYKSMKGL GTDDNTLIRV MVSRAEIDML DIRAHFKRLY GKSLYSFIKG
DTSGDYRKVL LVLCGGDD SEQ ID NO:7 - 60 kDa heat shock protein
MLRLPTVFRQ MRPVSRVLAP HLTRAYAKDV KFGADARALM LQGVDLLADA VAVTMGPKGR
TVIIEQSWGS PKVTKDGVTV AKSIDLKDKY KNIGAKLVQD VANNTNEEAG DGTTTATVLA
RSIAKEGFEK ISKGANPVEI RRGVMLAVDA VIAELKKQSK PVTTPEEIAQ VATISANGDK
EIGNIISDAM KKVGRKGVIT VKDGKTLNDE LEIIEGMKFD RGYISPYFIN TSKGQKCEFQ
DAYVLLSEKK ISSIQSIVPA LEIANAHRKP LVIIAEDVDG EALSTLVLNR LKVGLQVVAV
KAPGFGDNRK NQLKDMAIAT GGAVFGEEGL TLNLEDVQPH DLGKVGEVIV TKDDAMLLKG
KGDKAQIEKR IQEIIEQLDV TTSEYEKEKL NERLAKLSDG VAVLKVGGTS DVEVNEKKDR
VTDALNATRA AVEEGIVLGG GCALLRCIPA LDSLTPANED QKIGIEIIKR TLKIPAMTIA
KNAGVEGSLI VEKIMQSSSE VGYDAMAGDF VNMVEKGIID PTKVVRTALL DAAGVASLLT
TAEVVVTEIP KEEKDPGMGA MGGMGGGMGG GMF SEQ ID NO:8 - T complex protein 1 beta subunit
MASLSLAPVN IFKAGADEER AETARLTSFI GAIAIGDLVK STLGPKGMDK ILLSSGRDAS
LMVTNDGATI LKNIGVDNPA AKVLVDMSRV QDDEVGDGTT SVTVLAAELL REAESLIAKK
IHPQTIIAGW REATKAAREA LLSSAVDHGS DEVKFRQDLM NIAGTTLSSK LLTHHKDHFT
KLAVEAVLRL KGSGNLEAIH IIKKLGGSLA DSYLDEGFLL DKKIGVNQPK RIENAKILIA
NTGMDTDKIK IFGSRVRVDS TAKVAEIEHA EKEKMKEKVE RILKHGINCF INRQLIYNYP
EQLFGAAGVM AIEHADFAGV ERLALVTGGE IASTFDHPEL VKLGSCKLIE EVMIGEDKLI
HFSGVALGEA CTIVLRGATQ QILDEAERSL HDALCVLAQT VKDSRTVYGG GCSEMLMAHA
VTQLANRTPG KEAVAMESYA KALRMLPTII ADNAGYDSAD LVAQLRAAHS EGNTTAGLDM
REGTIGDMAI LGITESFQVK RQVLLSAAEA AEVILRVDNI IKAAPRKRVP DHHPC SEQ ID NO:9 - T complex protein 1 epsilon subunit
MASMGTLAFD EYGRPFLIIK DQDRKSRLMG LEALKSHIMA AKAVANTMRT SLGPNGLDKM
MVDKDGDVTV TNDGATILSM MDVDHQIAKL MVELSKSQDD EIGDGTTGVV VLAGALLEEA
EQLLDRGIHP IRIADGYEQA ARVAIEHLDK ISDSVLVDIK DTEPLIQTAK TTLGSKVVNS
CHRQMAEIAV NAVLTVADME RRDVDFELIK VEGKVGGRLE DTKLIKGVIV DKDFSHPQMP
KKVEDAKIAI LTCPFEPPKP KTKHKLDVTS VEDYKALQKY EKEKFEEMIQ QIKETGANLA
ICQWGFDDEA NHLLLQNNLP AVRWVGGPEI ELIAIATGGR IVPRFSELTA EKLGFAGLVQ
EISFGTTKDK MLVIEQCKNS RAVTIFIRGG NKMIIEEAKR SLHDALCVIR NLIRDNRVVY
```

-continued

GGGAAEISCA LAVSQEADKC PTLEQYAMRA FADALEVIPM ALSENSGMNP IQTMTEVRAR
QVKEMNPALG IDCLHKGTND MKQQHVIETL IGKKQQISLA TQMVRMILKI DDIRKPGESE
E

SEQ ID NO:10 - mortalin
MISASRAAAA RLVGAAASRG PTAARHQDSW NGLSHEAFRL VSRRDYASEA IKGAVVGIDL
GTTNSCVAVM EGKQAKVLEN AEGARTTPSV VAFTADGERL VGMPAKRQAV TNPNNTFYAT
KRLIGRRYDD PEVQKDIKNV PFKIVRASNG DAWVEAHGKL YSPSQIGAFV LMKMKETAEN
YLGHTAKNAV ITVPAYFNDS QRQATKDAGQ ISGLNVLRVI NEPTAAALAY GLDKSEDKVI
AVYDLGGGTF DISILEIQKG VFEVKSTNGD TFLGGEDFDQ ALLRHIVKEF KRETGVDLTK
DNMALQRVRE AAEKAKCELS SSVQTDINLP YLTMDSSGPK HLNMKLTRAQ FEGIVTDLIR
RTIAPCQKAM QDAEVSKSDI GEVILVGGMT RMPKVQQTVQ DLFGRAPSKA VNPDEAVAIG
AAIQGGVLAG DVTDVLLLDV TPLSLGIETL GGVFTKLINR NTTIPTKKSQ VFSTAADGQT
QVEIKVCQGE REMAGDNKLL GQFTLIGIPP APRGVPQIEV TFDIDANGIV HVSAKDKGTG
REQQIVIQSS GGLSKDDIEN MVKNAEKYAE EDRRKKERVE AVNMAEGIIH DTETKMEEFK
DQLPADECNK LKEEISKMRE LLARKDSETG ENIRQAASSL QQASLKLFEM AYKKMASERE
GSGSSGTGEQ KEDQKEEKQ SEQ ID NO:11 - TER-ATPase
MASGADSKGD DLSTAILKQK NRPNRLIVDE AINEDNSVVS LSQPRMDELQ LFRGDTVLLK
GKKRREAVCI VLSDDTCSDE KIRMNRVVRN NLRVRLGDVI SIQPCPDVKY GKRIHVLPID
DTVEGITGNL FEVYLKPYFL EAYRPIRKGD IFLVRGGMRA VEFKVVETDP SPYCIVAPDT
VIHCEGEPIK REDEEESLNE VGYDDIGGCR KQLAQIKEMV ELPLRHPALF KAIGVKPPRG
ILLYGPPGTG KTLIARAVAN ETGAFFFLIN GPEIMSKLAG ESESNLRKAF EEAEKNAPAI
IFIDELDAIA PKREKTHGEV ERRIVSQLLT LMDGLKQRAH VIVMAATNRP NSIDPALRRF
GRFDREVDIG IPDATGRLEI LQIHTKNMKL ADDVDLEQVA NETHGHVGAD LAALCSEAAL
QAIRKKMDLI DLEDETIDAE VMNSLAVTMD DFRWALSQSN PSALRETVVE VPQVTWEDIG
GLEDVKRELQ ELVQYPVEHP DKFLKFGMTP SKGVLFYGPP GCGKTLLAKA IANECQANFI
SIKGPELLTM WFGESEANVR EIFDKARQAA PCVLFFDELD SIAKARGGNI GDGGGAADRV
INQILTEMDG MSTKKNVFII GATNRPDIID PAILRPGRLD QLIYIPLPDE KSRVAILKAN
LRKSPVAKDV DLEFLAKMTN GFSGADLTEI CQRACKLAIR ESIESEIRRE RERQTNPSAM
EVEEDDPVPE IRRDHFEEAM RFARRSVSDN DIRKYEMFAQ TLQQSRGFGS RFRPSGNQGG
AGPSQGSGGG TGGSVYTEDN DDDLYG

The invention claimed is:

1. An in vitro method of identifying the presence of colorectal cancer cells in a test sample of tissue from an individual, said tissue comprising at least one of colon and rectal tissue, which method comprises:
   (a) determining whether a target protein is over-expressed in cells from said test sample compared to expression of the same protein in a second clinically normal tissue sample comprising at least one of colon and rectal tissue from the same individual or a second healthy individual, said target protein being mitochondrial stress-70 protein of SEQ ID NO: 10, and
   (b) correlating over-expression of said target protein with the presence of said cancer cells in said test sample, wherein over-expression of said protein indicates the presence of said cancer cell in said test sample.

2. A method as claimed in claim 1, wherein the target protein is detected using a recognition agent, said recognition agent being an antibody, or a binding moiety of an antibody, which is effective to specifically bind the target protein, and said recognition agent is optionally linked to a detectable label.

3. A method as claimed in claim 2 wherein the method comprises
   (a) obtaining from a patient a tissue sample comprising at least one of colon and rectal tissue to be tested for the presence of cancer cells;
   (b) producing a prepared sample of said tissue in a sample preparation process;
   (c) contacting the prepared sample with said recognition agent that binds to the target protein; and
   (d) detecting binding of the recognition agent to the target protein, if present, in the prepared sample.

4. A method as claimed in claim 2 wherein the recognition agent is an antibody.

* * * * *

SEQUENCE LISTING

<160> NUMBER OF SEQ ID NOS: 11

<210> SEQ ID NO 1
<211> LENGTH: 463
<212> TYPE: PRT
<213> ORGANISM: Homo sapiens
<220> FEATURE:
<223> OTHER INFORMATION: hnRNP-K

<400> SEQUENCE: 1

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
            20                  25                  30

Phe Lys Arg Ser Arg Asn Thr Asp Glu Met Val Glu Leu Arg Ile Leu
        35                  40                  45

Leu Gln Ser Lys Asn Ala Gly Ala Val Ile Gly Lys Gly Gly Lys Asn
    50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
        115                 120                 125

Ala Val Glu Cys Leu Asn Tyr Gln His Tyr Lys Gly Ser Asp Phe Asp
    130                 135                 140

```
Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
            165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
            195                 200                 205

Ile Leu Asp Leu Ile Ser Glu Ser Pro Ile Lys Gly Arg Ala Gln Pro
210                 215                 220

Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
            245                 250                 255

Gly Arg Gly Gly Phe Asp Arg Met Pro Pro Gly Arg Gly Gly Arg Pro
            260                 265                 270

Met Pro Pro Ser Arg Arg Asp Tyr Asp Asp Met Ser Pro Arg Arg Gly
            275                 280                 285

Pro Pro Pro Pro Pro Gly Arg Gly Gly Arg Gly Gly Ser Arg Ala
290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
            325                 330                 335

Val Gly Phe Ser Ala Asp Glu Thr Trp Asp Ser Ala Ile Asp Thr Trp
            340                 345                 350

Ser Pro Ser Glu Trp Gln Met Ala Tyr Glu Pro Gln Gly Gly Ser Gly
            355                 360                 365

Tyr Asp Tyr Ser Tyr Ala Gly Gly Arg Gly Ser Tyr Gly Asp Leu Gly
            370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
            405                 410                 415

Ser Gly Ala Ser Ile Lys Ile Asp Glu Pro Leu Glu Gly Ser Glu Asp
            420                 425                 430

Arg Ile Ile Thr Ile Thr Gly Thr Gln Asp Gln Ile Gln Asn Ala Gln
            435                 440                 445

Tyr Leu Leu Gln Asn Ser Val Lys Gln Tyr Ser Gly Lys Phe Phe
450                 455                 460

<210> SEQ ID NO 2
<211> LENGTH: 214
<212> TYPE: PRT
<213> ORGANISM: Homo sapiens
<220> FEATURE:
<223> OTHER INFORMATION: HMG-1

<400> SEQUENCE: 2

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45
```

```
Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Phe Lys Asp Pro Asn Ala Pro Lys Arg
            85                  90                  95

Pro Pro Ser Ala Phe Phe Leu Phe Cys Ser Glu Tyr Arg Pro Lys Ile
                100                 105                 110

Lys Gly Glu His Pro Gly Leu Ser Ile Gly Asp Val Ala Lys Lys Leu
                115                 120                 125

Gly Glu Met Trp Asn Asn Thr Ala Ala Asp Lys Gln Pro Tyr Glu
            130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Glu Glu Glu Asp Glu Glu Asp
                180                 185                 190

Glu Glu Asp Glu Glu Glu Glu Asp Glu Glu Asp Glu Asp Glu Glu
            195                 200                 205

Glu Asp Asp Asp Glu
            210

<210> SEQ ID NO 3
<211> LENGTH: 263
<212> TYPE: PRT
<213> ORGANISM: Homo sapiens
<220> FEATURE:
<223> OTHER INFORMATION: proteasome subunit alpha type 1

<400> SEQUENCE: 3

Met Phe Arg Asn Gln Tyr Asp Asn Asp Val Thr Val Trp Ser Pro Gln
1               5                   10                  15

Gly Arg Ile His Gln Ile Glu Tyr Ala Met Glu Ala Val Lys Gln Gly
            20                  25                  30

Ser Ala Thr Val Gly Leu Lys Ser Lys Thr His Ala Val Leu Val Ala
        35                  40                  45

Leu Lys Arg Ala Gln Ser Glu Leu Ala Ala His Gln Lys Lys Ile Leu
    50                  55                  60

His Val Asp Asn His Ile Gly Ile Ser Ile Ala Gly Leu Thr Ala Asp
65                  70                  75                  80

Ala Arg Leu Leu Cys Asn Phe Met Arg Gln Glu Cys Leu Asp Ser Arg
                85                  90                  95

Phe Val Phe Asp Arg Pro Leu Pro Val Ser Arg Leu Val Ser Leu Ile
                100                 105                 110

Gly Ser Lys Thr Gln Ile Pro Thr Gln Arg Tyr Gly Arg Arg Pro Tyr
            115                 120                 125

Gly Val Gly Leu Leu Ile Ala Gly Tyr Asp Asp Met Gly Pro His Ile
        130                 135                 140

Phe Gln Thr Cys Pro Ser Ala Asn Tyr Phe Asp Cys Arg Ala Met Ser
145                 150                 155                 160

Ile Gly Ala Arg Ser Gln Ser Ala Arg Thr Tyr Leu Glu Arg His Met
                165                 170                 175

Ser Glu Phe Met Glu Cys Asn Leu Asn Glu Leu Val Lys His Gly Leu
                180                 185                 190
```

```
Arg Ala Leu Arg Glu Thr Leu Pro Ala Glu Gln Asp Leu Thr Thr Lys
            195                 200                 205

Asn Val Ser Ile Gly Ile Val Gly Lys Asp Leu Glu Phe Thr Ile Tyr
            210                 215                 220

Asp Asp Asp Val Ser Pro Phe Leu Glu Gly Leu Glu Glu Arg Pro
225                 230                 235                 240

Gln Arg Lys Ala Gln Pro Ala Gln Pro Ala Asp Glu Pro Ala Glu Lys
            245                 250                 255

Ala Asp Glu Pro Met Glu His
            260

<210> SEQ ID NO 4
<211> LENGTH: 592
<212> TYPE: PRT
<213> ORGANISM: Homo sapiens
<220> FEATURE:
<223> OTHER INFORMATION: bifunctional purine biosynthesis protein

<400> SEQUENCE: 4

Met Ala Pro Gly Gln Leu Ala Leu Phe Ser Val Ser Asp Lys Thr Gly
1               5                   10                  15

Leu Val Glu Phe Ala Arg Asn Leu Thr Ala Leu Gly Leu Asn Leu Val
            20                  25                  30

Ala Ser Gly Gly Thr Ala Lys Ala Leu Arg Asp Ala Gly Leu Ala Val
            35                  40                  45

Arg Asp Val Ser Glu Leu Thr Gly Phe Pro Glu Met Leu Gly Gly Arg
50                  55                  60

Val Lys Thr Leu His Pro Ala Val His Ala Gly Ile Leu Ala Arg Asn
65                  70                  75                  80

Ile Pro Glu Asp Asn Ala Asp Met Ala Arg Leu Asp Phe Asn Leu Ile
                85                  90                  95

Arg Val Val Ala Cys Asn Leu Tyr Pro Phe Val Lys Thr Val Ala Ser
                100                 105                 110

Pro Gly Val Thr Val Glu Glu Ala Val Glu Gln Ile Asp Ile Gly Gly
            115                 120                 125

Val Thr Leu Leu Arg Ala Ala Ala Lys Asn His Ala Arg Val Thr Val
130                 135                 140

Val Cys Glu Pro Glu Asp Tyr Val Val Val Ser Thr Glu Met Gln Ser
145                 150                 155                 160

Ser Glu Ser Lys Asp Thr Ser Leu Glu Thr Arg Arg Gln Leu Ala Leu
                165                 170                 175

Lys Ala Phe Thr His Thr Ala Gln Tyr Asp Glu Ala Ile Ser Asp Tyr
            180                 185                 190

Phe Arg Lys Gln Tyr Ser Lys Gly Val Ser Gln Met Pro Leu Arg Tyr
            195                 200                 205

Gly Met Asn Pro His Gln Thr Pro Ala Gln Leu Tyr Thr Leu Gln Pro
            210                 215                 220

Lys Leu Pro Ile Thr Val Leu Asn Gly Ala Pro Gly Phe Ile Asn Leu
225                 230                 235                 240

Cys Asp Ala Leu Asn Ala Trp Gln Leu Val Lys Glu Leu Lys Glu Ala
                245                 250                 255

Leu Gly Ile Pro Ala Ala Ala Ser Phe Lys His Val Ser Pro Ala Gly
            260                 265                 270

Ala Ala Val Gly Ile Pro Leu Ser Glu Asp Glu Ala Lys Val Cys Met
            275                 280                 285
```

```
Val Tyr Asp Leu Tyr Lys Thr Leu Thr Pro Ile Ser Ala Ala Tyr Ala
    290                 295                 300

Arg Ala Arg Gly Ala Asp Arg Met Ser Ser Phe Gly Asp Phe Val Ala
305                 310                 315                 320

Leu Ser Asp Val Cys Asp Val Pro Thr Ala Lys Ile Ile Ser Arg Glu
                325                 330                 335

Val Ser Asp Gly Ile Ile Ala Pro Gly Tyr Glu Glu Ala Leu Thr
                340                 345                 350

Ile Leu Ser Lys Lys Lys Asn Gly Asn Tyr Cys Val Leu Gln Met Asp
                355                 360                 365

Gln Ser Tyr Lys Pro Asp Glu Asn Glu Val Arg Thr Leu Phe Gly Leu
    370                 375                 380

His Leu Ser Gln Lys Arg Asn Asn Gly Val Val Asp Lys Ser Leu Phe
385                 390                 395                 400

Ser Asn Val Val Thr Lys Asn Lys Asp Leu Pro Glu Ser Ala Leu Arg
                405                 410                 415

Asp Leu Ile Val Ala Thr Ile Ala Val Lys Tyr Thr Gln Ser Asn Ser
                420                 425                 430

Val Cys Tyr Ala Lys Asn Gly Gln Val Ile Gly Ile Gly Ala Gly Gln
                435                 440                 445

Gln Ser Arg Ile His Cys Thr Arg Leu Ala Gly Asp Lys Ala Asn Tyr
    450                 455                 460

Trp Trp Leu Arg His His Pro Gln Val Leu Ser Met Lys Phe Lys Thr
465                 470                 475                 480

Gly Val Lys Arg Ala Glu Ile Ser Asn Ala Ile Asp Gln Tyr Val Thr
                485                 490                 495

Gly Thr Ile Gly Glu Asp Glu Asp Leu Ile Lys Trp Lys Ala Leu Phe
                500                 505                 510

Glu Glu Val Pro Glu Leu Leu Thr Glu Ala Lys Lys Glu Trp Val
                515                 520                 525

Glu Lys Leu Thr Glu Val Ser Ile Ser Ser Asp Ala Phe Phe Pro Phe
    530                 535                 540

Arg Asp Asn Val Asp Arg Ala Lys Arg Ser Gly Val Ala Tyr Ile Ala
545                 550                 555                 560

Ala Pro Ser Gly Ser Ala Asp Lys Val Val Ile Glu Ala Cys Asp
                565                 570                 575

Glu Leu Gly Ile Ile Leu Ala His Thr Asn Leu Arg Leu Phe His His
                580                 585                 590

<210> SEQ ID NO 5
<211> LENGTH: 543
<212> TYPE: PRT
<213> ORGANISM: Homo sapiens
<220> FEATURE:
<223> OTHER INFORMATION: STI1

<400> SEQUENCE: 5

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
                20                  25                  30

Leu Asp Pro His Asn His Val Leu Tyr Ser Asn Arg Ser Ala Ala Tyr
                35                  40                  45

Ala Lys Lys Gly Asp Tyr Gln Lys Ala Tyr Glu Asp Gly Cys Lys Thr
    50                  55                  60
```

```
Val Asp Leu Lys Pro Asp Trp Gly Lys Gly Tyr Ser Arg Lys Ala Ala
 65                  70                  75                  80

Ala Leu Glu Phe Leu Asn Arg Phe Glu Glu Ala Lys Arg Thr Tyr Glu
                 85                  90                  95

Glu Gly Leu Lys His Glu Ala Asn Asn Pro Gln Leu Lys Glu Gly Leu
            100                 105                 110

Gln Asn Met Glu Ala Arg Leu Ala Glu Arg Lys Phe Met Asn Pro Phe
        115                 120                 125

Asn Met Pro Asn Leu Tyr Gln Lys Leu Glu Ser Asp Pro Arg Thr Arg
    130                 135                 140

Thr Leu Leu Ser Asp Pro Thr Tyr Arg Glu Leu Ile Glu Gln Leu Arg
145                 150                 155                 160

Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
            180                 185                 190

Glu Glu Glu Ile Ala Thr Pro Pro Pro Pro Pro Lys Lys Glu
        195                 200                 205

Thr Lys Pro Glu Pro Met Glu Glu Asp Leu Pro Glu Asn Lys Lys Gln
    210                 215                 220

Ala Leu Lys Glu Lys Glu Leu Gly Asn Asp Ala Tyr Lys Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
            260                 265                 270

Gly Asp Tyr Asn Lys Cys Arg Glu Leu Cys Glu Lys Ala Ile Glu Val
        275                 280                 285

Gly Arg Glu Asn Arg Glu Asp Tyr Arg Gln Ile Ala Lys Ala Tyr Ala
    290                 295                 300

Arg Ile Gly Asn Ser Tyr Phe Lys Glu Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
        355                 360                 365

Glu Cys Phe Gln Lys Gly Asp Tyr Pro Gln Ala Met Lys His Tyr Thr
    370                 375                 380

Glu Ala Ile Lys Arg Asn Pro Lys Asp Ala Lys Leu Tyr Ser Asn Arg
385                 390                 395                 400

Ala Ala Cys Tyr Thr Lys Leu Leu Glu Phe Gln Leu Ala Leu Lys Asp
                405                 410                 415

Cys Glu Glu Cys Ile Gln Leu Glu Pro Thr Phe Ile Lys Gly Tyr Thr
            420                 425                 430

Arg Lys Ala Ala Ala Leu Glu Ala Met Lys Asp Tyr Thr Lys Ala Met
        435                 440                 445

Asp Val Tyr Gln Lys Ala Leu Asp Leu Asp Ser Ser Cys Lys Glu Ala
    450                 455                 460

Ala Asp Gly Tyr Gln Arg Cys Met Met Ala Gln Tyr Asn Arg His Asp
465                 470                 475                 480
```

```
Ser Pro Glu Asp Val Lys Arg Arg Ala Met Ala Asp Pro Glu Val Gln
            485                 490                 495

Gln Ile Met Ser Asp Pro Ala Met Arg Leu Ile Leu Glu Gln Met Gln
            500                 505                 510

Lys Asp Pro Gln Ala Leu Ser Glu His Leu Lys Asn Pro Val Ile Ala
            515                 520                 525

Gln Lys Ile Gln Lys Leu Met Asp Val Gly Leu Ile Ala Ile Arg
            530                 535                 540

<210> SEQ ID NO 6
<211> LENGTH: 318
<212> TYPE: PRT
<213> ORGANISM: Homo sapiens
<220> FEATURE:
<223> OTHER INFORMATION: annexin IV

<400> SEQUENCE: 6

Ala Thr Lys Gly Gly Thr Val Lys Ala Ala Ser Gly Phe Asn Ala Met
1               5                   10                  15

Glu Asp Ala Gln Thr Leu Arg Lys Ala Met Lys Gly Leu Gly Thr Asp
            20                  25                  30

Glu Asp Ala Ile Ile Ser Val Leu Ala Tyr Arg Asn Thr Ala Gln Arg
        35                  40                  45

Gln Glu Ile Arg Thr Ala Tyr Lys Ser Thr Ile Gly Arg Asp Leu Ile
    50                  55                  60

Asp Asp Leu Lys Ser Glu Leu Ser Gly Asn Phe Glu Gln Val Ile Val
65                  70                  75                  80

Gly Met Met Thr Pro Thr Val Leu Tyr Asp Val Gln Glu Leu Arg Arg
                85                  90                  95

Ala Met Lys Gly Ala Gly Thr Asp Glu Gly Cys Leu Ile Glu Ile Leu
            100                 105                 110

Ala Ser Arg Thr Pro Glu Glu Ile Arg Arg Ile Ser Gln Thr Tyr Gln
        115                 120                 125

Gln Gln Tyr Gly Arg Ser Leu Glu Asp Asp Ile Arg Ser Asp Thr Ser
    130                 135                 140

Phe Met Phe Gln Arg Val Leu Val Ser Leu Ser Ala Gly Gly Arg Asp
145                 150                 155                 160

Glu Gly Asn Tyr Leu Asp Asp Ala Leu Val Arg Gln Asp Ala Gln Asp
                165                 170                 175

Leu Tyr Glu Ala Gly Glu Lys Lys Trp Gly Thr Asp Glu Val Lys Phe
            180                 185                 190

Leu Thr Val Leu Cys Ser Arg Asn Arg Asn His Leu Leu His Val Phe
        195                 200                 205

Asp Glu Tyr Lys Arg Ile Ser Gln Lys Asp Ile Glu Gln Ser Ile Lys
    210                 215                 220

Ser Glu Thr Ser Gly Ser Phe Glu Asp Ala Leu Leu Ala Ile Val Lys
225                 230                 235                 240

Cys Met Arg Asn Lys Ser Ala Tyr Phe Ala Glu Lys Leu Tyr Lys Ser
                245                 250                 255

Met Lys Gly Leu Gly Thr Asp Asp Asn Thr Leu Ile Arg Val Met Val
            260                 265                 270

Ser Arg Ala Glu Ile Asp Met Leu Asp Ile Arg Ala His Phe Lys Arg
        275                 280                 285

Leu Tyr Gly Lys Ser Leu Tyr Ser Phe Ile Lys Gly Asp Thr Ser Gly
    290                 295                 300
```

```
Asp Tyr Arg Lys Val Leu Leu Val Leu Cys Gly Gly Asp Asp
305                 310                 315
```

```
<210> SEQ ID NO 7
<211> LENGTH: 573
<212> TYPE: PRT
<213> ORGANISM: Homo sapiens
<220> FEATURE:
<223> OTHER INFORMATION: 60 kDa heat shock protein

<400> SEQUENCE: 7

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350
```

-continued

```
Asp Asp Ala Met Leu Lys Gly Lys Gly Asp Lys Ala Gln Ile Glu
        355                 360                 365
Lys Arg Ile Gln Glu Ile Ile Glu Gln Leu Asp Val Thr Thr Ser Glu
    370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Gly Cys Ala Leu Leu Arg Cys Ile
        435                 440                 445
Pro Ala Leu Asp Ser Leu Thr Pro Ala Asn Glu Asp Gln Lys Ile Gly
    450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
        515                 520                 525
Leu Leu Asp Ala Ala Gly Val Ala Ser Leu Leu Thr Thr Ala Glu Val
    530                 535                 540
Val Val Thr Glu Ile Pro Lys Glu Glu Lys Asp Pro Gly Met Gly Ala
545                 550                 555                 560
Met Gly Gly Met Gly Gly Gly Met Gly Gly Gly Met Phe
                565                 570
```

<210> SEQ ID NO 8
<211> LENGTH: 535
<212> TYPE: PRT
<213> ORGANISM: Homo sapiens
<220> FEATURE:
<223> OTHER INFORMATION: T complex protein 1 beta subunit

<400> SEQUENCE: 8

```
Met Ala Ser Leu Ser Leu Ala Pro Val Asn Ile Phe Lys Ala Gly Ala
1               5                   10                  15
Asp Glu Glu Arg Ala Glu Thr Ala Arg Leu Thr Ser Phe Ile Gly Ala
            20                  25                  30
Ile Ala Ile Gly Asp Leu Val Lys Ser Thr Leu Gly Pro Lys Gly Met
        35                  40                  45
Asp Lys Ile Leu Leu Ser Ser Gly Arg Asp Ala Ser Leu Met Val Thr
    50                  55                  60
Asn Asp Gly Ala Thr Ile Leu Lys Asn Ile Gly Val Asp Asn Pro Ala
65                  70                  75                  80
Ala Lys Val Leu Val Asp Met Ser Arg Val Gln Asp Asp Glu Val Gly
                85                  90                  95
Asp Gly Thr Thr Ser Val Thr Val Leu Ala Ala Glu Leu Leu Arg Glu
            100                 105                 110
Ala Glu Ser Leu Ile Ala Lys Lys Ile His Pro Gln Thr Ile Ile Ala
        115                 120                 125
Gly Trp Arg Glu Ala Thr Lys Ala Ala Arg Glu Ala Leu Leu Ser Ser
    130                 135                 140
```

```
Ala Val Asp His Gly Ser Asp Glu Val Lys Phe Arg Gln Asp Leu Met
145                 150                 155                 160

Asn Ile Ala Gly Thr Thr Leu Ser Ser Lys Leu Leu Thr His His Lys
                165                 170                 175

Asp His Phe Thr Lys Leu Ala Val Glu Ala Val Leu Arg Leu Lys Gly
            180                 185                 190

Ser Gly Asn Leu Glu Ala Ile His Ile Ile Lys Lys Leu Gly Gly Ser
        195                 200                 205

Leu Ala Asp Ser Tyr Leu Asp Glu Gly Phe Leu Leu Asp Lys Lys Ile
    210                 215                 220

Gly Val Asn Gln Pro Lys Arg Ile Glu Asn Ala Lys Ile Leu Ile Ala
225                 230                 235                 240

Asn Thr Gly Met Asp Thr Asp Lys Ile Lys Ile Phe Gly Ser Arg Val
                245                 250                 255

Arg Val Asp Ser Thr Ala Lys Val Ala Glu Ile Glu His Ala Glu Lys
            260                 265                 270

Glu Lys Met Lys Glu Lys Val Glu Arg Ile Leu Lys His Gly Ile Asn
        275                 280                 285

Cys Phe Ile Asn Arg Gln Leu Ile Tyr Asn Tyr Pro Glu Gln Leu Phe
    290                 295                 300

Gly Ala Ala Gly Val Met Ala Ile Glu His Ala Asp Phe Ala Gly Val
305                 310                 315                 320

Glu Arg Leu Ala Leu Val Thr Gly Gly Glu Ile Ala Ser Thr Phe Asp
                325                 330                 335

His Pro Glu Leu Val Lys Leu Gly Ser Cys Lys Leu Ile Glu Glu Val
            340                 345                 350

Met Ile Gly Glu Asp Lys Leu Ile His Phe Ser Gly Val Ala Leu Gly
        355                 360                 365

Glu Ala Cys Thr Ile Val Leu Arg Gly Ala Thr Gln Gln Ile Leu Asp
    370                 375                 380

Glu Ala Glu Arg Ser Leu His Asp Ala Leu Cys Val Leu Ala Gln Thr
385                 390                 395                 400

Val Lys Asp Ser Arg Thr Val Tyr Gly Gly Cys Ser Glu Met Leu
                405                 410                 415

Met Ala His Ala Val Thr Gln Leu Ala Asn Arg Thr Pro Gly Lys Glu
            420                 425                 430

Ala Val Ala Met Glu Ser Tyr Ala Lys Ala Leu Arg Met Leu Pro Thr
        435                 440                 445

Ile Ile Ala Asp Asn Ala Gly Tyr Asp Ser Ala Asp Leu Val Ala Gln
    450                 455                 460

Leu Arg Ala Ala His Ser Glu Gly Asn Thr Thr Ala Gly Leu Asp Met
465                 470                 475                 480

Arg Glu Gly Thr Ile Gly Asp Met Ala Ile Leu Gly Ile Thr Glu Ser
                485                 490                 495

Phe Gln Val Lys Arg Gln Val Leu Leu Ser Ala Ala Glu Ala Ala Glu
            500                 505                 510

Val Ile Leu Arg Val Asp Asn Ile Ile Lys Ala Ala Pro Arg Lys Arg
        515                 520                 525

Val Pro Asp His His Pro Cys
530                 535

<210> SEQ ID NO 9
<211> LENGTH: 541
<212> TYPE: PRT
```

```
<213> ORGANISM: Homo sapiens
<220> FEATURE:
<223> OTHER INFORMATION: T complex protein 1 epsilon subunit

<400> SEQUENCE: 9

Met Ala Ser Met Gly Thr Leu Ala Phe Asp Glu Tyr Gly Arg Pro Phe
1               5                   10                  15

Leu Ile Ile Lys Asp Gln Asp Arg Lys Ser Arg Leu Met Gly Leu Glu
            20                  25                  30

Ala Leu Lys Ser His Ile Met Ala Ala Lys Ala Val Ala Asn Thr Met
        35                  40                  45

Arg Thr Ser Leu Gly Pro Asn Gly Leu Asp Lys Met Met Val Asp Lys
50                  55                  60

Asp Gly Asp Val Thr Val Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
            100                 105                 110

Ala Gly Ala Leu Leu Glu Glu Ala Glu Gln Leu Leu Asp Arg Gly Ile
        115                 120                 125

His Pro Ile Arg Ile Ala Asp Gly Tyr Glu Gln Ala Ala Arg Val Ala
130                 135                 140

Ile Glu His Leu Asp Lys Ile Ser Asp Ser Val Leu Val Asp Ile Lys
145                 150                 155                 160

Asp Thr Glu Pro Leu Ile Gln Thr Ala Lys Thr Thr Leu Gly Ser Lys
                165                 170                 175

Val Val Asn Ser Cys His Arg Gln Met Ala Glu Ile Ala Val Asn Ala
            180                 185                 190

Val Leu Thr Val Ala Asp Met Glu Arg Arg Asp Val Asp Phe Glu Leu
        195                 200                 205

Ile Lys Val Glu Gly Lys Val Gly Gly Arg Leu Glu Asp Thr Lys Leu
210                 215                 220

Ile Lys Gly Val Ile Val Asp Lys Asp Phe Ser His Pro Gln Met Pro
225                 230                 235                 240

Lys Lys Val Glu Asp Ala Lys Ile Ala Ile Leu Thr Cys Pro Phe Glu
                245                 250                 255

Pro Pro Lys Pro Lys Thr Lys His Lys Leu Asp Val Thr Ser Val Glu
            260                 265                 270

Asp Tyr Lys Ala Leu Gln Lys Tyr Glu Lys Glu Lys Phe Glu Glu Met
        275                 280                 285

Ile Gln Gln Ile Lys Glu Thr Gly Ala Asn Leu Ala Ile Cys Gln Trp
290                 295                 300

Gly Phe Asp Asp Glu Ala Asn His Leu Leu Leu Gln Asn Asn Leu Pro
305                 310                 315                 320

Ala Val Arg Trp Val Gly Gly Pro Glu Ile Glu Leu Ile Ala Ile Ala
                325                 330                 335

Thr Gly Gly Arg Ile Val Pro Arg Phe Ser Glu Leu Thr Ala Glu Lys
            340                 345                 350

Leu Gly Phe Ala Gly Leu Val Gln Glu Ile Ser Phe Gly Thr Thr Lys
        355                 360                 365

Asp Lys Met Leu Val Ile Glu Gln Cys Lys Asn Ser Arg Ala Val Thr
370                 375                 380

Ile Phe Ile Arg Gly Gly Asn Lys Met Ile Ile Glu Glu Ala Lys Arg
```

```
                385                 390                 395                 400
Ser Leu His Asp Ala Leu Cys Val Ile Arg Asn Leu Ile Arg Asp Asn
                    405                 410                 415

Arg Val Val Tyr Gly Gly Gly Ala Ala Glu Ile Ser Cys Ala Leu Ala
                420                 425                 430

Val Ser Gln Glu Ala Asp Lys Cys Pro Thr Leu Glu Gln Tyr Ala Met
            435                 440                 445

Arg Ala Phe Ala Asp Ala Leu Glu Val Ile Pro Met Ala Leu Ser Glu
        450                 455                 460

Asn Ser Gly Met Asn Pro Ile Gln Thr Met Thr Glu Val Arg Ala Arg
465                 470                 475                 480

Gln Val Lys Glu Met Asn Pro Ala Leu Gly Ile Asp Cys Leu His Lys
                485                 490                 495

Gly Thr Asn Asp Met Lys Gln Gln His Val Ile Glu Thr Leu Ile Gly
                500                 505                 510

Lys Lys Gln Gln Ile Ser Leu Ala Thr Gln Met Val Arg Met Ile Leu
                515                 520                 525

Lys Ile Asp Asp Ile Arg Lys Pro Gly Glu Ser Glu Glu
                530                 535                 540

<210> SEQ ID NO 10
<211> LENGTH: 679
<212> TYPE: PRT
<213> ORGANISM: Homo sapiens
<220> FEATURE:
<223> OTHER INFORMATION: mortalin

<400> SEQUENCE: 10

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Arg Asp Tyr Ala Ser
            35                  40                  45

Glu Ala Ile Lys Gly Ala Val Val Gly Ile Asp Leu Gly Thr Thr Asn
        50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
                100                 105                 110

Pro Asn Asn Thr Phe Tyr Ala Thr Lys Arg Leu Ile Gly Arg Arg Tyr
            115                 120                 125

Asp Asp Pro Glu Val Gln Lys Asp Ile Lys Asn Val Pro Phe Lys Ile
        130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
                180                 185                 190

Val Pro Ala Tyr Phe Asn Asp Ser Gln Arg Gln Ala Thr Lys Asp Ala
            195                 200                 205

Gly Gln Ile Ser Gly Leu Asn Val Leu Arg Val Ile Asn Glu Pro Thr
```

-continued

```
           210                 215                 220
Ala Ala Ala Leu Ala Tyr Gly Leu Asp Lys Ser Glu Asp Lys Val Ile
225                 230                 235                 240

Ala Val Tyr Asp Leu Gly Gly Thr Phe Asp Ile Ser Ile Leu Glu
            245                 250                 255

Ile Gln Lys Gly Val Phe Glu Val Lys Ser Thr Asn Gly Asp Thr Phe
                260                 265                 270

Leu Gly Gly Glu Asp Phe Asp Gln Ala Leu Leu Arg His Ile Val Lys
            275                 280                 285

Glu Phe Lys Arg Glu Thr Gly Val Asp Leu Thr Lys Asp Asn Met Ala
290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
            405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
            435                 440                 445

Thr Leu Gly Gly Val Phe Thr Lys Leu Ile Asn Arg Asn Thr Thr Ile
            450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
530                 535                 540

Ile Val Ile Gln Ser Ser Gly Gly Leu Ser Lys Asp Ile Glu Asn
545                 550                 555                 560

Met Val Lys Asn Ala Glu Lys Tyr Ala Glu Glu Asp Arg Arg Lys Lys
            565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
            610                 615                 620

Lys Asp Ser Glu Thr Gly Glu Asn Ile Arg Gln Ala Ala Ser Ser Leu
625                 630                 635                 640
```

-continued

Gln Gln Ala Ser Leu Lys Leu Phe Glu Met Ala Tyr Lys Lys Met Ala
                645                 650                 655

Ser Glu Arg Glu Gly Ser Gly Ser Gly Thr Gly Glu Gln Lys Glu
            660                 665                 670

Asp Gln Lys Glu Glu Lys Gln
        675

<210> SEQ ID NO 11
<211> LENGTH: 806
<212> TYPE: PRT
<213> ORGANISM: Homo sapiens
<220> FEATURE:
<223> OTHER INFORMATION: TER-ATPase

<400> SEQUENCE: 11

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
305                 310                 315                 320

-continued

```
Glu Arg Arg Ile Val Ser Gln Leu Leu Thr Leu Met Asp Gly Leu Lys
            325                 330                 335
Gln Arg Ala His Val Ile Val Met Ala Ala Thr Asn Arg Pro Asn Ser
        340                 345                 350
Ile Asp Pro Ala Leu Arg Arg Phe Gly Arg Phe Asp Arg Glu Val Asp
    355                 360                 365
Ile Gly Ile Pro Asp Ala Thr Gly Arg Leu Glu Ile Leu Gln Ile His
370                 375                 380
Thr Lys Asn Met Lys Leu Ala Asp Asp Val Asp Leu Glu Gln Val Ala
385                 390                 395                 400
Asn Glu Thr His Gly His Val Gly Ala Asp Leu Ala Ala Leu Cys Ser
            405                 410                 415
Glu Ala Ala Leu Gln Ala Ile Arg Lys Lys Met Asp Leu Ile Asp Leu
        420                 425                 430
Glu Asp Glu Thr Ile Asp Ala Glu Val Met Asn Ser Leu Ala Val Thr
    435                 440                 445
Met Asp Asp Phe Arg Trp Ala Leu Ser Gln Ser Asn Pro Ser Ala Leu
450                 455                 460
Arg Glu Thr Val Val Glu Val Pro Gln Val Thr Trp Glu Asp Ile Gly
465                 470                 475                 480
Gly Leu Glu Asp Val Lys Arg Glu Leu Gln Glu Leu Val Gln Tyr Pro
            485                 490                 495
Val Glu His Pro Asp Lys Phe Leu Lys Phe Gly Met Thr Pro Ser Lys
        500                 505                 510
Gly Val Leu Phe Tyr Gly Pro Pro Gly Cys Gly Lys Thr Leu Leu Ala
    515                 520                 525
Lys Ala Ile Ala Asn Glu Cys Gln Ala Asn Phe Ile Ser Ile Lys Gly
530                 535                 540
Pro Glu Leu Leu Thr Met Trp Phe Gly Glu Ser Glu Ala Asn Val Arg
545                 550                 555                 560
Glu Ile Phe Asp Lys Ala Arg Gln Ala Ala Pro Cys Val Leu Phe Phe
            565                 570                 575
Asp Glu Leu Asp Ser Ile Ala Lys Ala Arg Gly Gly Asn Ile Gly Asp
        580                 585                 590
Gly Gly Gly Ala Ala Asp Arg Val Ile Asn Gln Ile Leu Thr Glu Met
    595                 600                 605
Asp Gly Met Ser Thr Lys Lys Asn Val Phe Ile Ile Gly Ala Thr Asn
610                 615                 620
Arg Pro Asp Ile Ile Asp Pro Ala Ile Leu Arg Pro Gly Arg Leu Asp
625                 630                 635                 640
Gln Leu Ile Tyr Ile Pro Leu Pro Asp Glu Lys Ser Arg Val Ala Ile
            645                 650                 655
Leu Lys Ala Asn Leu Arg Lys Ser Pro Val Ala Lys Asp Val Asp Leu
        660                 665                 670
Glu Phe Leu Ala Lys Met Thr Asn Gly Phe Ser Gly Ala Asp Leu Thr
    675                 680                 685
Glu Ile Cys Gln Arg Ala Cys Lys Leu Ala Ile Arg Glu Ser Ile Glu
690                 695                 700
Ser Glu Ile Arg Arg Glu Arg Glu Arg Gln Thr Asn Pro Ser Ala Met
705                 710                 715                 720
Glu Val Glu Glu Asp Asp Pro Val Pro Glu Ile Arg Arg Asp His Phe
            725                 730                 735
```

```
Glu Glu Ala Met Arg Phe Ala Arg Arg Ser Val Ser Asp Asn Asp Ile
            740             745             750

Arg Lys Tyr Glu Met Phe Ala Gln Thr Leu Gln Gln Ser Arg Gly Phe
        755             760             765

Gly Ser Phe Arg Phe Pro Ser Gly Asn Gln Gly Gly Ala Gly Pro Ser
        770             775             780

Gln Gly Ser Gly Gly Gly Thr Gly Gly Ser Val Tyr Thr Glu Asp Asn
785             790             795             800

Asp Asp Asp Leu Tyr Gly
            805
```